(12) United States Patent
Adney et al.

(10) Patent No.: US 7,375,197 B2
(45) Date of Patent: May 20, 2008

(54) CELLOBIOHYDROLASE I GENE AND IMPROVED VARIANTS

(75) Inventors: William S. Adney, Golden, CO (US); Stephen R. Decker, Berthoud, CO (US); Suzanne Mc Carter, San Carlos, CA (US); John O. Baker, Golden, CO (US); Raphael Nieves, Lakewood, CO (US); Michael E. Himmel, Littleton, CO (US); Todd B. Vinzant, Golden, CO (US)

(73) Assignee: MidWest Research Institute, Kansas City, MO (US)

( * ) Notice: Subject to any disclaimer, the term of this patent is extended or adjusted under 35 U.S.C. 154(b) by 238 days.

(21) Appl. No.: 10/031,496

(22) Filed: Jan. 14, 2002

(65) Prior Publication Data

US 2003/0170861 A1    Sep. 11, 2003

(51) Int. Cl.
*C07H 21/04* (2006.01)
(52) U.S. Cl. .................................... 536/23.1
(58) Field of Classification Search ............... 536/23.2, 536/23.1; 435/4, 6, 69.1, 183, 252.3
See application file for complete search history.

(56) References Cited

U.S. PATENT DOCUMENTS

| | | | |
|---|---|---|---|
| 4,472,504 A | 9/1984 | Gallo | |
| 5,298,405 A | 3/1994 | Nevalanen et al. | |
| 5,874,276 A * | 2/1999 | Fowler et al. | 435/209 |
| 5,989,870 A * | 11/1999 | Nakari et al. | 435/91.1 |
| 6,011,147 A * | 1/2000 | Nakari et al. | 536/24.1 |
| 6,114,296 A | 9/2000 | Schulein et al. | |

FOREIGN PATENT DOCUMENTS

| | | | |
|---|---|---|---|
| EP | 0133035 A2 | | 2/1985 |
| EP | 0 137 280 A | | 4/1985 |
| WO | WO 94/04673 | * | 3/1994 |
| WO | WO 01/04284 A1 | * | 1/2001 |

OTHER PUBLICATIONS

Godbole, S., et al. (1999) Biotechnol. Prog. 15, 828-833.*
Srisodsuk, M., et al.(1993) J. Biol. Chem. 268(28), 20756-20761.*
Basco, et al., "Selective elongation of the oligosaccharide attached to the second potential glycosylation site of yeast exoglucanase: effects of the activity and properties of the enzyme," Biochemical Journal, Portland Press, London, GB, vol. 304, No. 3, Dec. 15, 1994, pp. 917-922.
Harrison, et al., "Modified glycosylation of cellobiohydrolase I from a high cellulase-producing mutant strain of trichoderma reesei," European Journal of Biochemistry, vol. 256, No. 1, Aug. 1998, pp. 119-127.
Maras et al., "In vitro conversion of the carbohydrate moiety of fungal glycoproteins to mammalian-type oligosaccharides," European Journal of Biochemistry, Berlin, DE, vol. 249, 1997, pp. 701-707.

* cited by examiner

*Primary Examiner*—Robert B. Mondesi
(74) *Attorney, Agent, or Firm*—Paul J. White; Kenneth Richardson; Mark D. Trenner

(57) ABSTRACT

The disclosure provides a method for preparing an active exoglucanase in a heterologous host of eukaryotic origin. The method includes mutagenesis to reduce glycosylation of the exoglucanase when expressed in a heterologous host. It is further disclosed a method to produce variant cellobiohydrolase that is stable at high temperature through mutagenesis.

20 Claims, 4 Drawing Sheets

Coding sequence of the *cbh 1* gene (SEQ ID NO: 4). Lower case letters represent the signal sequence, upper case letters the catalytic domain, bolded italics the linker region, and upper case underlined the cellulose-binding domain.

atgtatcggaagttggccgtcatctcggccttcttggccacagctcgtgctCAGTCGGCCTGCACTCTCCAATCGGA
GACTCACCCGCCTCTGACATGGCAGAAATGCTCGTCTGGTGGCACGTGCACTCAACA
GACAGGCTCCGTGGTCATCGACGCCAACTGGCGCTGGACTCACGCTACGAAC
AGCAGCACGAACTGCTACGATGGCAACACTTGGAGCTCGACCCTATGTCCTG
ACAACGAGACCTGCGCGAAGAACTGCTGTCTGGACGGTGCCGCCTACGCGTC
CACGTACGGAGTTACCACGAGCGGTAACAGCCTCTCCATTGGCTTTGTCACCC
AGTCTGCGCAGAAGAACGTTGGCGCTCGCCTTTACCTTATGGCGAGCGACAC
GACCTACCAGGAATTCACCCTGCTTGGCAACGAGTTCTCTTTCGATGTTGATG
TTTCGCAGCTGCCGTGCGGCTTGAACGGAGCTCTCTACTTCGTGTCCATGGAC
GCGGATGGTGGCGTGAGCAAGTATCCCACCAACACCGCTGGCGCCAAGTACG
GCACGGGGTACTGTGACAGCCAGTGTCCCGCGATCTGAAGTTCATCAATGG
CCAGGCCAACGTTGAGGGCTGGGAGCCGTCATCCAACAACGCGAACACGGG
CATTGGAGGACACGGAAGCTGCTGCTCTGAGATGGATATCTGGGAGGCCAAC
TCCATCTCCGAGGCTCTTACCCCCCACCCTTGCACGACTGTCGGCCAGGAGAT
CTGCGAGGGTGATGGGTGCGGCGGAACTTACTCCGATAACAGATATGGCGGC
ACTTGCGATCCCGATGGCTGCGACTGGAACCCATACCGCCTGGGCAACACCA
GCTTCTACGGCCCTGGCTCAAGCTTTACCCTCGATACCACCAAGAAATTGACC
GTTGTCACCCAGTTCGAGACGTCGGGTGCCATCAACCGATACTATGTCCAGA
ATGGCGTCACTTTCCAGCAGCCCAACGCCGAGCTTGGTAGTTACTCTGGCAA
CGAGCTCAACGATGATTACTGCACAGCTGAGGAGGCAGAATTCGGCGGATCC
TCTTTCTCAGACAAGGGCGGCCTGACTCAGTTCAAGAAGGCTACCTCTGGCG
GCATGGTTCTGGTCATGAGTCTGTGGGATGATTACTACGCCAACATGCTGTGG
CTGGACTCCACCTACCCGACAAACGAGACCTCCTCCACACCCGGTGCCGTGC
GCGGAAGCTGCTCCACCAGCTCCGGTGTCCCTGCTCAGGTCGAATCTCAGTCT
CCCAACGCCAAGGTCACCTTCTCCAACATCAAGTTCGGACCCATTGGCAGCA
CCGGCAACCCTAGCGGCGGCAAC*CCTCCCGGCGGAAACCCGCCTGGCACCAC*
*CACCACCCGCCGCCCAGCCACTACCACTGGAAGCTCTCCCGGACCT*<u>ACCCAGT</u>
<u>CTCACTACGGCCAGTGCGGCGGTATTGGCTACAGCGGCCCCACGGTCTGCGC</u>
<u>CAGCGGCACAACTTGCCAGGTCCTGAACCCTTACTACTCTCAGTGCCTGTAAA</u>
<u>GCTCC</u>

Figure 1

SDS-PAGE western blot using anti-CBH I showing the reduction in molecular weight of rCBH I expression clones as a function of the introduction of N>A modifications.

Figure 2

Plasmid map of fungal expression vector pPFE2/CBHI

Nucleotide sequence SEQ ID NO: 1, 5'-CCTCCCGGCGGAAACCCGCCTGGCACCACCACCACCCGCCGCCCA-3', coding for the linker region, PPGGNPPGTTTTRRP (SEQ ID NO: 2), of the CBH I protein, showing additional proline residues that effect conformation of the linker region in the protein structure.

SEQUENCE LISTING

<160> NUMBER OF SEQ ID NOS: 99

<210> SEQ ID NO 1
<211> LENGTH: 45
<212> TYPE: DNA
<213> ORGANISM: Artificial
<220> FEATURE:
<223> OTHER INFORMATION: Nucleotide encoding linker

<400> SEQUENCE: 1
cctcccggcg gaaacccgcc tggcaccacc accacccgcc gccca                45

<210> SEQ ID NO 2
<211> LENGTH: 15
<212> TYPE: PRT
<213> ORGANISM: Trichoderma reesei

<400> SEQUENCE: 2

Pro Pro Gly Gly Asn Pro Pro Gly Thr Thr Thr Thr Arg Arg Pro
1               5                   10                  15

<210> SEQ ID NO 3
<211> LENGTH: 24
<212> TYPE: DNA
<213> ORGANISM: Artificial sequence
<220> FEATURE:
<223> OTHER INFORMATION: Nucleotide encoding linker

<400> SEQUENCE: 3
ggcggaaacc cgcctggcac cacc                                       24

<210> SEQ ID NO 4
<211> LENGTH: 1551
<212> TYPE: DNA
<213> ORGANISM: Trichoderma reesei

<400> SEQUENCE: 4
atgtatcgga agttggccgt catctcggcc ttcttggcca cagctcgtgc tcagtcggcc    60
tgcactctcc aatcggagac tcacccgcct ctgacatggc agaaatgctc gtctggtggc    120
acgtgcactc aacagacagg ctccgtggtc atcgacgcca actggcgctg gactcacgct    180
acgaacagca gcacgaactg ctacgatggc aacacttgga gctcgaccct atgtcctgac    240
aacgagacct cgcgaagaa ctgctgtctg acggtgccg cctacgcgtc cacgtacgga    300
gttaccacga gcggtaacag cctctccatt ggctttgtca cccagtctgc gcagaagaac    360
gttggcgctc gcctttacct tatggcgagc gacacgacct accaggaatt cacccctgctt    420
ggcaacgagt tctctttcga tgttgatgtt tcgcagctgc cgtgcggctt gaacggagct    480
ctctacttcg tgtccatgga cgcggatggt ggcgtgagca agtatcccac caacaccgct    540
ggcgccaagt acggcacggg gtactgtgac agccagtgtc ccgcgatct gaagttcatc    600
aatggccagg ccaacgttga gggctgggag ccgtcatcca caacgcgaa cacgggcatt    660
ggaggacacg gaagctgctg ctctgagatg gatatctggg aggccaactc catctccgag    720
gctcttaccc cccaccttg cacgactgtc ggccaggaga tctgcgaggg tgatgggtgc    780
ggcggaactt actccgataa cagatatggc ggcacttgcg atcccgatgg ctgcgactgg    840
aaccatatac cgctgggcaa caccagcttc tacggccctg gctcaagctt taccctcgat    900
accaccaaga aattgaccgt tgtcacccag ttcgagacgt cgggtgccat caaccgatac    960

-continued

```
tatgtccaga atggcgtcac tttccagcag cccaacgccg agcttggtag ttactctggc   1020
aacgagctca acgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
aacgagacct cctccacacc cggtgccgtg cgcggaagct gctccaccag ctccggtgtc   1260
cctgctcagg tcgaatctca gtctcccaac gccaaggtca ccttctccaa catcaagttc   1320
ggacccattg gcagcaccgg caaccctagc ggcggcaacc ctcccggcgg aaacccgcct   1380
ggcaccacca ccaccgccg cccagccact accactggaa gctctcccgg acctacccag   1440
tctcactacg ccagtgcgg cggtattggc tacagcggcc ccacggtctg cgccagcggc   1500
acaacttgcc aggtcctgaa cccttactac tctcagtgcc tgtaaagctc c            1551
```

<210> SEQ ID NO 5
<211> LENGTH: 514
<212> TYPE: PRT
<213> ORGANISM: Trichoderma reesei

<400> SEQUENCE: 5

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270
```

```
Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
        290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
        370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
        450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 6
<211> LENGTH: 514
<212> TYPE: PRT
<213> ORGANISM: Trichoderma reesei CBH1-N45A

<400> SEQUENCE: 6

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Ala Ser Ser
        50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125
```

```
Ala Ser Asp Thr Thr Tyr Gln Glu Phe Thr Leu Leu Gly Asn Glu Phe
        130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 7
<211> LENGTH: 514
<212> TYPE: PRT
<213> ORGANISM: Trichoderma reesei CBH1-N270A
```

<400> SEQUENCE: 7

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Ala Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
```

-continued

```
                405                 410                 415
Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
            450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510

Cys Leu

<210> SEQ ID NO 8
<211> LENGTH: 514
<212> TYPE: PRT
<213> ORGANISM: Trichoderma reesei CBH1-N384A

<400> SEQUENCE: 8

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
            50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
            85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
            130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
            165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
```

-continued

```
                260                 265                 270
Cys Asp Pro Asp Gly Cys Asp Trp Asn Pro Tyr Arg Leu Gly Asn Thr
            275                 280                 285
Ser Phe Tyr Gly Pro Gly Ser Ser Phe Thr Leu Asp Thr Thr Lys Lys
        290                 295                 300
Leu Thr Val Val Thr Gln Phe Glu Thr Ser Gly Ala Ile Asn Arg Tyr
305                 310                 315                 320
Tyr Val Gln Asn Gly Val Thr Phe Gln Gln Pro Asn Ala Glu Leu Gly
                325                 330                 335
Ser Tyr Ser Gly Asn Glu Leu Asn Asp Asp Tyr Cys Thr Ala Glu Glu
            340                 345                 350
Ala Glu Phe Gly Gly Ser Ser Phe Ser Asp Lys Gly Gly Leu Thr Gln
        355                 360                 365
Phe Lys Lys Ala Thr Ser Gly Gly Met Val Leu Val Met Ser Leu Trp
    370                 375                 380
Asp Asp Tyr Tyr Ala Asn Met Leu Trp Leu Asp Ser Thr Tyr Pro Thr
385                 390                 395                 400
Ala Glu Thr Ser Ser Thr Pro Gly Ala Val Arg Gly Ser Cys Ser Thr
                405                 410                 415
Ser Ser Gly Val Pro Ala Gln Val Glu Ser Gln Ser Pro Asn Ala Lys
            420                 425                 430
Val Thr Phe Ser Asn Ile Lys Phe Gly Pro Ile Gly Ser Thr Gly Asn
        435                 440                 445
Pro Ser Gly Gly Asn Pro Pro Gly Gly Asn Pro Pro Gly Thr Thr Thr
    450                 455                 460
Thr Arg Arg Pro Ala Thr Thr Thr Gly Ser Ser Pro Gly Pro Thr Gln
465                 470                 475                 480
Ser His Tyr Gly Gln Cys Gly Gly Ile Gly Tyr Ser Gly Pro Thr Val
                485                 490                 495
Cys Ala Ser Gly Thr Thr Cys Gln Val Leu Asn Pro Tyr Tyr Ser Gln
            500                 505                 510
Cys Leu

<210> SEQ ID NO 9
<211> LENGTH: 28
<212> TYPE: DNA
<213> ORGANISM: Artificial
<220> FEATURE:
<223> OTHER INFORMATION: Primer for PCR

<400> SEQUENCE: 9
agagagtcta gacacggagc ttacaggc                                        28

<210> SEQ ID NO 10
<211> LENGTH: 26
<212> TYPE: DNA
<213> ORGANISM: Artificial
<220> FEATURE:
<223> OTHER INFORMATION: S8P Native sense strand

<400> SEQUENCE: 10
gcactctcca atcggagact cacccg                                          26

<210> SEQ ID NO 11
<211> LENGTH: 26
<212> TYPE: DNA
<213> ORGANISM: Artificial
<220> FEATURE:
```

```
<223> OTHER INFORMATION: S8P Mutagenic sense strand

<400> SEQUENCE: 11
gcactctcca accggagact cacccg                                          26

<210> SEQ ID NO 12
<211> LENGTH: 26
<212> TYPE: DNA
<213> ORGANISM: Artificial
<220> FEATURE:
<223> OTHER INFORMATION: S8P Mutagenic anti-sense strand

<400> SEQUENCE: 12
cgggtgagtc tccggttgga gagtgc                                          26

<210> SEQ ID NO 13
<211> LENGTH: 28
<212> TYPE: DNA
<213> ORGANISM: Artificial
<220> FEATURE:
<223> OTHER INFORMATION: N27P Native sense strand

<400> SEQUENCE: 13
ggcacgtgca ctcaacagac aggctccg                                        28

<210> SEQ ID NO 14
<211> LENGTH: 28
<212> TYPE: DNA
<213> ORGANISM: Artificial
<220> FEATURE:
<223> OTHER INFORMATION: N27P Mutagenic sense strand

<400> SEQUENCE: 14
ggcacgtgca ctccacagac aggctccg                                        28

<210> SEQ ID NO 15
<211> LENGTH: 28
<212> TYPE: DNA
<213> ORGANISM: Artificial
<220> FEATURE:
<223> OTHER INFORMATION: N27P Mutagenic anti-sense strand

<400> SEQUENCE: 15
cggagcctgt ctgtggagtg cacgtgcc                                        28

<210> SEQ ID NO 16
<211> LENGTH: 32
<212> TYPE: DNA
<213> ORGANISM: Artificial
<220> FEATURE:
<223> OTHER INFORMATION: A43P Native sense strand

<400> SEQUENCE: 16
ggcgctggac tcacgctacg aacagcagca cg                                   32

<210> SEQ ID NO 17
<211> LENGTH: 32
<212> TYPE: DNA
<213> ORGANISM: Artificial
<220> FEATURE:
<223> OTHER INFORMATION: A43P Mutagenic sense strand

<400> SEQUENCE: 17
ggcgctggac tcaccctacg aacagcagca cg                                   32
```

<210> SEQ ID NO 18
<211> LENGTH: 32
<212> TYPE: DNA
<213> ORGANISM: Artificial
<220> FEATURE:
<223> OTHER INFORMATION: A43P Mutagenic anti-sense strand

<400> SEQUENCE: 18
cgtgctgctg ttcgtagggt gagtccagcg cc                                32

<210> SEQ ID NO 19
<211> LENGTH: 26
<212> TYPE: DNA
<213> ORGANISM: Artificial
<220> FEATURE:
<223> OTHER INFORMATION: G75P native sense strand

<400> SEQUENCE: 19
gctgtctgga cggtgccgcc tacgcg                                       26

<210> SEQ ID NO 20
<211> LENGTH: 26
<212> TYPE: DNA
<213> ORGANISM: Artificial
<220> FEATURE:
<223> OTHER INFORMATION: G74P Mutagenic sense strand

<400> SEQUENCE: 20
gctgtctgga ccctgccgcc tacgcg                                       26

<210> SEQ ID NO 21
<211> LENGTH: 26
<212> TYPE: DNA
<213> ORGANISM: Artificial
<220> FEATURE:
<223> OTHER INFORMATION: G75P Mutagenic anti-sense strand

<400> SEQUENCE: 21
cgcgtaggcg gcagggtcca gacagc                                       26

<210> SEQ ID NO 22
<211> LENGTH: 24
<212> TYPE: DNA
<213> ORGANISM: Artificial
<220> FEATURE:
<223> OTHER INFORMATION: G94P Native sense strand

<400> SEQUENCE: 22
gcctctccat tggctttgtc accc                                         24

<210> SEQ ID NO 23
<211> LENGTH: 24
<212> TYPE: DNA
<213> ORGANISM: Artificial
<220> FEATURE:
<223> OTHER INFORMATION: G94P Mutagenic sense strand

<400> SEQUENCE: 23
gcctctccat tccctttgtc accc                                         24

<210> SEQ ID NO 24
<211> LENGTH: 24
<212> TYPE: DNA
<213> ORGANISM: Artificial
<220> FEATURE:
<223> OTHER INFORMATION: G94P Mutagenic anti-sense strand

```
<400> SEQUENCE: 24
gggtgacaaa gggaatggag aggc                                          24

<210> SEQ ID NO 25
<211> LENGTH: 24
<212> TYPE: DNA
<213> ORGANISM: Artificial
<220> FEATURE:
<223> OTHER INFORMATION: E190P Native sense strand

<400> SEQUENCE: 25
ggccaacgtt gagggctggg agcc                                          24

<210> SEQ ID NO 26
<211> LENGTH: 24
<212> TYPE: DNA
<213> ORGANISM: Artificial
<220> FEATURE:
<223> OTHER INFORMATION: E190P Mutagenic sense strand

<400> SEQUENCE: 26
ggccaacgtt ccgggctggg agcc                                          24

<210> SEQ ID NO 27
<211> LENGTH: 24
<212> TYPE: DNA
<213> ORGANISM: Artificial
<220> FEATURE:
<223> OTHER INFORMATION: E190 Mutagenic anti-sense strand

<400> SEQUENCE: 27
ggctcccagc ccggaacgtt ggcc                                          24

<210> SEQ ID NO 28
<211> LENGTH: 27
<212> TYPE: DNA
<213> ORGANISM: Artificial
<220> FEATURE:
<223> OTHER INFORMATION: S195P Native sense strand

<400> SEQUENCE: 28
ggctgggagc cgtcatccaa caacgcg                                       27

<210> SEQ ID NO 29
<211> LENGTH: 27
<212> TYPE: DNA
<213> ORGANISM: Artificial
<220> FEATURE:
<223> OTHER INFORMATION: S195P Mutagenic sense strand

<400> SEQUENCE: 29
ggctgggagc cgccatccaa caacgcg                                       27

<210> SEQ ID NO 30
<211> LENGTH: 27
<212> TYPE: DNA
<213> ORGANISM: Artificial
<220> FEATURE:
<223> OTHER INFORMATION: S195P Mutagenic anti-sense strand

<400> SEQUENCE: 30
cgcgttgttg gatggcggct cccagcc                                       27

<210> SEQ ID NO 31
<211> LENGTH: 32
```

```
<212> TYPE: DNA
<213> ORGANISM: Artificial
<220> FEATURE:
<223> OTHER INFORMATION: K287P Native sense strand

<400> SEQUENCE: 31
cgataccacc aagaaattga ccgttgtcac cc                              32

<210> SEQ ID NO 32
<211> LENGTH: 32
<212> TYPE: DNA
<213> ORGANISM: Artificial
<220> FEATURE:
<223> OTHER INFORMATION: K287P Mutagenic sense strand

<400> SEQUENCE: 32
cgataccacc aagccattga ccgttgtcac cc                              32

<210> SEQ ID NO 33
<211> LENGTH: 32
<212> TYPE: DNA
<213> ORGANISM: Artificial
<220> FEATURE:
<223> OTHER INFORMATION: K287P Mutagenic anti-sense strand

<400> SEQUENCE: 33
gggtgacaac ggtcaatggc ttggtggtat cg                              32

<210> SEQ ID NO 34
<211> LENGTH: 28
<212> TYPE: DNA
<213> ORGANISM: Artificial
<220> FEATURE:
<223> OTHER INFORMATION: A299P Native sense strand

<400> SEQUENCE: 34
cgagacgtcg ggtgccatca accgatac                                   28

<210> SEQ ID NO 35
<211> LENGTH: 28
<212> TYPE: DNA
<213> ORGANISM: Artificial
<220> FEATURE:
<223> OTHER INFORMATION: A299P Mutagenic sense strand

<400> SEQUENCE: 35
cgagacgtcg ggtcccatca accgatac                                   28

<210> SEQ ID NO 36
<211> LENGTH: 28
<212> TYPE: DNA
<213> ORGANISM: Artificial
<220> FEATURE:
<223> OTHER INFORMATION: A299P Mutagenic anti-sense strand

<400> SEQUENCE: 36
gtatcggttg atgggacccg acgtctcg                                   28

<210> SEQ ID NO 37
<211> LENGTH: 35
<212> TYPE: DNA
<213> ORGANISM: Artificial
<220> FEATURE:
<223> OTHER INFORMATION: Q312P/N315P Native sense strand

<400> SEQUENCE: 37
```
ggcgtcactt tccagcagcc caacgccgag cttgg                35

<210> SEQ ID NO 38
<211> LENGTH: 35
<212> TYPE: DNA
<213> ORGANISM: Artificial
<220> FEATURE:
<223> OTHER INFORMATION: Q312P/N315P Mutagenic sense strand

<400> SEQUENCE: 38
ggcgtcactt tcccgcagcc ccccgccgag cttgg                35

<210> SEQ ID NO 39
<211> LENGTH: 35
<212> TYPE: DNA
<213> ORGANISM: Artificial
<220> FEATURE:
<223> OTHER INFORMATION: Q312P/N315P Mutagenic anti-sense strand

<400> SEQUENCE: 39
ccaagctcgg cgggggctg cgggaaagtg acgcc                35

<210> SEQ ID NO 40
<211> LENGTH: 26
<212> TYPE: DNA
<213> ORGANISM: Artificial
<220> FEATURE:
<223> OTHER INFORMATION: G359P Native sense strand

<400> SEQUENCE: 40
ggctacctct ggcggcatgg ttctgg                          26

<210> SEQ ID NO 41
<211> LENGTH: 26
<212> TYPE: DNA
<213> ORGANISM: Artificial
<220> FEATURE:
<223> OTHER INFORMATION: G359P Mutagenic sense strand

<400> SEQUENCE: 41
ggctacctct cccggcatgg ttctgg                          26

<210> SEQ ID NO 42
<211> LENGTH: 26
<212> TYPE: DNA
<213> ORGANISM: Artificial
<220> FEATURE:
<223> OTHER INFORMATION: G359P Mutagenic anti-sense strand

<400> SEQUENCE: 42
ccagaaccat gccgggagag gtagcc                          26

<210> SEQ ID NO 43
<211> LENGTH: 34
<212> TYPE: DNA
<213> ORGANISM: Artificial
<220> FEATURE:
<223> OTHER INFORMATION: S398P/S401P Native sense strand

<400> SEQUENCE: 43
gcggaagctg ctccaccagc tccggtgtcc ctgc                 34

<210> SEQ ID NO 44
<211> LENGTH: 34
<212> TYPE: DNA
<213> ORGANISM: Artificial

```
<220> FEATURE:
<223> OTHER INFORMATION: S398P/S410P Mutagenic sense strand

<400> SEQUENCE: 44
gcggaagctg ccccaccagc cccggtgtcc ctgc                          34

<210> SEQ ID NO 45
<211> LENGTH: 34
<212> TYPE: DNA
<213> ORGANISM: Artificial
<220> FEATURE:
<223> OTHER INFORMATION: S398P/S401P Mutagenic anti-sense strand

<400> SEQUENCE: 45
gcagggacac cggggctggt ggggcagctt ccgc                          34

<210> SEQ ID NO 46
<211> LENGTH: 22
<212> TYPE: DNA
<213> ORGANISM: Artificial
<220> FEATURE:
<223> OTHER INFORMATION: A414P Native sense strand

<400> SEQUENCE: 46
gtctcccaac gccaaggtca cc                                       22

<210> SEQ ID NO 47
<211> LENGTH: 22
<212> TYPE: DNA
<213> ORGANISM: Artificial
<220> FEATURE:
<223> OTHER INFORMATION: A414P Mutagenic sense strand

<400> SEQUENCE: 47
gtctcccaac cccaaggtca cc                                       22

<210> SEQ ID NO 48
<211> LENGTH: 22
<212> TYPE: DNA
<213> ORGANISM: Artificial
<220> FEATURE:
<223> OTHER INFORMATION: A414P Mutagenic anti-sense strand

<400> SEQUENCE: 48
ggtgaccttg ggttgggag ac                                        22

<210> SEQ ID NO 49
<211> LENGTH: 32
<212> TYPE: DNA
<213> ORGANISM: Artificial
<220> FEATURE:
<223> OTHER INFORMATION: N431P/S433P Native sense strand

<400> SEQUENCE: 49
ggcagcaccg gcaaccctag cggcggcaac cc                            32

<210> SEQ ID NO 50
<211> LENGTH: 32
<212> TYPE: DNA
<213> ORGANISM: Artificial
<220> FEATURE:
<223> OTHER INFORMATION: N431P/S433P Mutagenic sense strand

<400> SEQUENCE: 50
ggcagcaccg gcccccctcc cggcggcaac cc                            32
```

```
<210> SEQ ID NO 51
<211> LENGTH: 32
<212> TYPE: DNA
<213> ORGANISM: Artificial
<220> FEATURE:
<223> OTHER INFORMATION: N431P/S433P Mutagenic anti-sense strand

<400> SEQUENCE: 51
gggttgccgc cgggaggggg gccggtgctg cc                               32

<210> SEQ ID NO 52
<211> LENGTH: 36
<212> TYPE: DNA
<213> ORGANISM: Artificial
<220> FEATURE:
<223> OTHER INFORMATION: S99G Native sense strand

<400> SEQUENCE: 52
ggctttgtca cccagtctgc gcagaagaac gttggc                           36

<210> SEQ ID NO 53
<211> LENGTH: 36
<212> TYPE: DNA
<213> ORGANISM: Artificial
<220> FEATURE:
<223> OTHER INFORMATION: S99G Mutagenic sense strand

<400> SEQUENCE: 53
ggctttgtca cccagggtgc gcagaagaac gttggc                           36

<210> SEQ ID NO 54
<211> LENGTH: 36
<212> TYPE: DNA
<213> ORGANISM: Artificial
<220> FEATURE:
<223> OTHER INFORMATION: S99G Mutagenic anti-sense strand

<400> SEQUENCE: 54
gccaacgttc ttctgcgcac cctgggtgac aaagcc                           36

<210> SEQ ID NO 55
<211> LENGTH: 20
<212> TYPE: DNA
<213> ORGANISM: Artificial
<220> FEATURE:
<223> OTHER INFORMATION: R251A Native sense strand

<400> SEQUENCE: 55
ccgataacag atatggcggc                                             20

<210> SEQ ID NO 56
<211> LENGTH: 20
<212> TYPE: DNA
<213> ORGANISM: Artificial
<220> FEATURE:
<223> OTHER INFORMATION: R251A Mutagenic sense strand

<400> SEQUENCE: 56
ccgataacgc ctatggcggc                                             20

<210> SEQ ID NO 57
<211> LENGTH: 20
<212> TYPE: DNA
<213> ORGANISM: Artificial
<220> FEATURE:
<223> OTHER INFORMATION: R251A Mutagenic anti-sense strand
```

<400> SEQUENCE: 57
gccgccatag gcgttatcgg                                           20

<210> SEQ ID NO 58
<211> LENGTH: 30
<212> TYPE: DNA
<213> ORGANISM: Artificial
<220> FEATURE:
<223> OTHER INFORMATION: R394A Native sense strand

<400> SEQUENCE: 58
cccggtgccg tgcgcggaag ctgctccacc                                30

<210> SEQ ID NO 59
<211> LENGTH: 30
<212> TYPE: DNA
<213> ORGANISM: Artificial
<220> FEATURE:
<223> OTHER INFORMATION: R394A Mutagenic sense strand

<400> SEQUENCE: 59
cccggtgccg tggccggaag ctgctccacc                                30

<210> SEQ ID NO 60
<211> LENGTH: 30
<212> TYPE: DNA
<213> ORGANISM: Artificial
<220> FEATURE:
<223> OTHER INFORMATION: R394A Mutagenic anti-sense strand

<400> SEQUENCE: 60
ggtggagcag cttccggcca cggcaccggg                                30

<210> SEQ ID NO 61
<211> LENGTH: 35
<212> TYPE: DNA
<213> ORGANISM: Artificial
<220> FEATURE:
<223> OTHER INFORMATION: F338A Native sense strand

<400> SEQUENCE: 61
gctgaggagg cagaattcgg cggatcctct ttctc                          35

<210> SEQ ID NO 62
<211> LENGTH: 35
<212> TYPE: DNA
<213> ORGANISM: Artificial
<220> FEATURE:
<223> OTHER INFORMATION: F338A Mutagenic sense strand

<400> SEQUENCE: 62
gctgaggagg cagaagccgg cggatcctct ttctc                          35

<210> SEQ ID NO 63
<211> LENGTH: 35
<212> TYPE: DNA
<213> ORGANISM: Artificial
<220> FEATURE:
<223> OTHER INFORMATION: F338A Mutagenic anti-sense strand

<400> SEQUENCE: 63
gagaaagagg atccgccggc ttctgcctcc tcagc                          35

<210> SEQ ID NO 64

```
<210> SEQ ID NO 64
<211> LENGTH: 29
<212> TYPE: DNA
<213> ORGANISM: Artificial
<220> FEATURE:
<223> OTHER INFORMATION: R267A Native sense strand

<400> SEQUENCE: 64
ggaacccata ccgcctgggc aacaccagc                                    29

<210> SEQ ID NO 65
<211> LENGTH: 29
<212> TYPE: DNA
<213> ORGANISM: Artificial
<220> FEATURE:
<223> OTHER INFORMATION: R267A Mutagenic sense strand

<400> SEQUENCE: 65
ggaacccata cgccctgggc aacaccagc                                    29

<210> SEQ ID NO 66
<211> LENGTH: 29
<212> TYPE: DNA
<213> ORGANISM: Artificial
<220> FEATURE:
<223> OTHER INFORMATION: R267A Mutagenic anti-sense strand

<400> SEQUENCE: 66
gctggtgttg cccagggcgt atgggttcc                                    29

<210> SEQ ID NO 67
<211> LENGTH: 34
<212> TYPE: DNA
<213> ORGANISM: Artificial
<220> FEATURE:
<223> OTHER INFORMATION: E285A Native sense strand

<400> SEQUENCE: 67
cctacccgac aaacgagacc tcctccacac ccgg                              34

<210> SEQ ID NO 68
<211> LENGTH: 34
<212> TYPE: DNA
<213> ORGANISM: Artificial
<220> FEATURE:
<223> OTHER INFORMATION: E385A Mutagenic sense strand

<400> SEQUENCE: 68
cctacccgac aaacgccacc tcctccacac ccgg                              34

<210> SEQ ID NO 69
<211> LENGTH: 34
<212> TYPE: DNA
<213> ORGANISM: Artificial
<220> FEATURE:
<223> OTHER INFORMATION: E385A Mutagenic anti-sense strand

<400> SEQUENCE: 69
ccgggtgtgg aggaggtggc gtttgtcggg tagg                              34

<210> SEQ ID NO 70
<211> LENGTH: 32
<212> TYPE: DNA
<213> ORGANISM: Artificial
<220> FEATURE:
<223> OTHER INFORMATION: N45A Native sense strand

<400> SEQUENCE: 70
```

```
ggactcacgc tacggccagc agcacgaact gc                                32

<210> SEQ ID NO 71
<211> LENGTH: 32
<212> TYPE: DNA
<213> ORGANISM: Artificial
<220> FEATURE:
<223> OTHER INFORMATION: N45A Mutagenic sense strand

<400> SEQUENCE: 71
ggactcacgc tacgaacagc agcacgaact gc                                32

<210> SEQ ID NO 72
<211> LENGTH: 32
<212> TYPE: DNA
<213> ORGANISM: Artificial
<220> FEATURE:
<223> OTHER INFORMATION: N45A Mutagenic anti-sense strand

<400> SEQUENCE: 72
gcagttcgtg ctgctggccg tagcgtgagt cc                                32

<210> SEQ ID NO 73
<211> LENGTH: 36
<212> TYPE: DNA
<213> ORGANISM: Artificial
<220> FEATURE:
<223> OTHER INFORMATION: N270A Native sense strand

<400> SEQUENCE: 73
cccataccgc ctgggcaaca ccagcttcta cggccc                            36

<210> SEQ ID NO 74
<211> LENGTH: 36
<212> TYPE: DNA
<213> ORGANISM: Artificial
<220> FEATURE:
<223> OTHER INFORMATION: N270A Mutagenic sense strand

<400> SEQUENCE: 74
cccataccgc ctgggcgcca ccagcttcta cggccc                            36

<210> SEQ ID NO 75
<211> LENGTH: 36
<212> TYPE: DNA
<213> ORGANISM: Artificial
<220> FEATURE:
<223> OTHER INFORMATION: N270A Mutagenic anti-sense strand

<400> SEQUENCE: 75
gggccgtaga agctggtggc gcccaggcgg tatggg                            36

<210> SEQ ID NO 76
<211> LENGTH: 41
<212> TYPE: DNA
<213> ORGANISM: Artificial
<220> FEATURE:
<223> OTHER INFORMATION: N384A Native sense strand

<400> SEQUENCE: 76
ggactccacc tacccgacaa acgagacctc ctccacaccc g                      41

<210> SEQ ID NO 77
<211> LENGTH: 41
<212> TYPE: DNA
```

<213> ORGANISM: Artificial
<220> FEATURE:
<223> OTHER INFORMATION: N384A Mutagenic sense strand

<400> SEQUENCE: 77
ggactccacc tacccgacag ccgagacctc ctccacaccc g                    41

<210> SEQ ID NO 78
<211> LENGTH: 41
<212> TYPE: DNA
<213> ORGANISM: Artificial
<220> FEATURE:
<223> OTHER INFORMATION: N384A Mutagenic anti-sense strand

<400> SEQUENCE: 78
cgggtgtgga ggaggtctcg gctgtcgggt aggtggagtc c                    41

<210> SEQ ID NO 79
<211> LENGTH: 23
<212> TYPE: DNA
<213> ORGANISM: Artificial
<220> FEATURE:
<223> OTHER INFORMATION: E337R Native sense strand

<400> SEQUENCE: 79
gctgaggagg cagaattcgg cgg                                        23

<210> SEQ ID NO 80
<211> LENGTH: 23
<212> TYPE: DNA
<213> ORGANISM: Artificial
<220> FEATURE:
<223> OTHER INFORMATION: E337R Mutagenic sense strand

<400> SEQUENCE: 80
gctgaggagg cacgcttcgg cgg                                        23

<210> SEQ ID NO 81
<211> LENGTH: 23
<212> TYPE: DNA
<213> ORGANISM: Artificial
<220> FEATURE:
<223> OTHER INFORMATION: E337R Mutagenic anti-sense strand

<400> SEQUENCE: 81
ccgccgaagc gtgcctcctc agc                                        23

<210> SEQ ID NO 82
<211> LENGTH: 27
<212> TYPE: DNA
<213> ORGANISM: Artificial
<220> FEATURE:
<223> OTHER INFORMATION: N327D Native sense strand

<400> SEQUENCE: 82
ggcaacgagc tcaacgatga ttactgc                                    27

<210> SEQ ID NO 83
<211> LENGTH: 27
<212> TYPE: DNA
<213> ORGANISM: Artificial
<220> FEATURE:
<223> OTHER INFORMATION: N327D Mutagenic sense strand

<400> SEQUENCE: 83
ggcaacgagc tcgacgatga ttactgc                                    27

<210> SEQ ID NO 84
<211> LENGTH: 27
<212> TYPE: DNA
<213> ORGANISM: Artificial
<220> FEATURE:
<223> OTHER INFORMATION: N327D Mutagenic anti-sense strand

<400> SEQUENCE: 84
gcagtaatca tcgtcgagct cgttgcc                                    27

<210> SEQ ID NO 85
<211> LENGTH: 35
<212> TYPE: DNA
<213> ORGANISM: Artificial
<220> FEATURE:
<223> OTHER INFORMATION: A405D Native sense strand

<400> SEQUENCE: 85
ccggtgtccc tgctcaggtc gaatctcagt ctccc                           35

<210> SEQ ID NO 86
<211> LENGTH: 35
<212> TYPE: DNA
<213> ORGANISM: Artificial
<220> FEATURE:
<223> OTHER INFORMATION: A405D Mutagenic sense strand

<400> SEQUENCE: 86
ccggtgtccc tgatcaggtc gaatctcagt ctccc                           35

<210> SEQ ID NO 87
<211> LENGTH: 35
<212> TYPE: DNA
<213> ORGANISM: Artificial
<220> FEATURE:
<223> OTHER INFORMATION: A405D Mutagenic anti-sense strand

<400> SEQUENCE: 87
gggagactga gattcgacct gatcagggac accgg                           35

<210> SEQ ID NO 88
<211> LENGTH: 30
<212> TYPE: DNA
<213> ORGANISM: Artificial
<220> FEATURE:
<223> OTHER INFORMATION: Q410R Native sense strand

<400> SEQUENCE: 88
gctcaggtcg aatctcagtc tcccaacgcc                                 30

<210> SEQ ID NO 89
<211> LENGTH: 30
<212> TYPE: DNA
<213> ORGANISM: Artificial
<220> FEATURE:
<223> OTHER INFORMATION: Q410R Mutagenic sense strand

<400> SEQUENCE: 89
gctcaggtcg aatctcgctc tcccaacgcc                                 30

<210> SEQ ID NO 90
<211> LENGTH: 30
<212> TYPE: DNA
<213> ORGANISM: Artificial
<220> FEATURE:

<223> OTHER INFORMATION: Q410R Mutagenic anti-sense strand

<400> SEQUENCE: 90
ggcgttggga gagcgagatt cgacctgagc					30

<210> SEQ ID NO 91
<211> LENGTH: 29
<212> TYPE: DNA
<213> ORGANISM: Artificial
<220> FEATURE:
<223> OTHER INFORMATION: N64D Native sense strand

<400> SEQUENCE: 91
ccctatgtcc tgacaacgag acctgcgcg					29

<210> SEQ ID NO 92
<211> LENGTH: 29
<212> TYPE: DNA
<213> ORGANISM: Artificial
<220> FEATURE:
<223> OTHER INFORMATION: N64D Mutagenic sense strand

<400> SEQUENCE: 92
ccctatgtcc tgacgacgag acctgcgcg					29

<210> SEQ ID NO 93
<211> LENGTH: 29
<212> TYPE: DNA
<213> ORGANISM: Artificial
<220> FEATURE:
<223> OTHER INFORMATION: N64D Mutagenic anti-sense strand

<400> SEQUENCE: 93
cgcgcaggtc tcgtcgtcag gacatagggg				29

<210> SEQ ID NO 94
<211> LENGTH: 44
<212> TYPE: DNA
<213> ORGANISM: Artificial
<220> FEATURE:
<223> OTHER INFORMATION: N64D Native sense strand

<400> SEQUENCE: 94
gctcgaccct atgtcctgac aacgagacct gcgcgaagaa ctgc				44

<210> SEQ ID NO 95
<211> LENGTH: 44
<212> TYPE: DNA
<213> ORGANISM: Artificial
<220> FEATURE:
<223> OTHER INFORMATION: N64D Mutagenic sense strand

<400> SEQUENCE: 95
gctcgaccct atgtcctgac gacgagacct gcgcgaagaa ctgc				44

<210> SEQ ID NO 96
<211> LENGTH: 44
<212> TYPE: DNA
<213> ORGANISM: Artificial
<220> FEATURE:
<223> OTHER INFORMATION: N64D Mutagenic anti-sense strand

<400> SEQUENCE: 96
gcagttcttc gcgcaggtct cgtcgtcagg acatagggtc gagc				44

<210> SEQ ID NO 97
<211> LENGTH: 35
<212> TYPE: DNA
<213> ORGANISM: Artificial
<220> FEATURE:
<223> OTHER INFORMATION: Primer

<400> SEQUENCE: 97
aaagaagcgc ggccgcgcct gcactctcca atcgg                              35

<210> SEQ ID NO 98
<211> LENGTH: 1500
<212> TYPE: DNA
<213> ORGANISM: Trichoderma reesei

<400> SEQUENCE: 98
cagtcggcct gcactctcca atcggagact cacccgcctc tgacatggca gaaatgctcg    60
tctggtggca cgtgcactca acagacaggc tccgtggtca tcgacgccaa ctggcgctgg   120
actcacgcta cgaacagcag cacgaactgc tacgatggca cacttggag ctcgacccta    180 tgtcctgaca cgagacctg cgcgaagaac tgctgtctgg acggtgccgc ctacgcgtcc    240
acgtacggag ttaccacgag cggtaacagc ctctccattg gctttgtcac ccagtctgcg   300
cagaagaacg ttggcgctcg cctttacctt atggcgagcg acacgaccta ccaggaattc   360
accctgcttg gcaacgagtt ctctttcgat gttgatgttt cgcagctgcc gtgcggcttg   420
aacggagctc tctacttcgt gtccatggac gcggatggtg gcgtgagcaa gtatcccacc   480
aacaccgctg gcgccaagta cggcacgggg tactgtgaca ccagtgtcc ccgcgatctg    540 aagttcatca atggccaggc caacgttgag ggctgggagc cgtcatccaa caacgcgaac   600
acgggcattg gaggacacgg aagctgctgc tctgagatgg atatctggga ggccaactcc   660
atctccgagg ctcttacccc ccaccttgc acgactgtcg ccaggagat ctgcgagggt     720 gatgggtgcg gcggaactta ctccgataac agatatggcg gcacttgcga tcccgatggc   780
tgcgactgga cccataccg cctgggcaac accagcttct acggccctgg ctcaagcttt   840
accctcgata ccaccaagaa attgaccgtt gtcacccagt cgagacgtc gggtgccatc    900 aaccgatact atgtccagaa tggcgtcact ttccagcagc ccaacgccga gcttggtagt   960
tactctggca cgagctcaa cgatgattac tgcacagctg aggaggcaga attcggcgga  1020 tcctcttct cagacaaggg cggcctgact cagttcaaga aggctacctc tggcggcatg  1080
gttctggtca tgagtctgtg ggatgattac tacgccaaca tgctgtggct ggactccacc  1140
tacccgacaa acgagacctc ctccacaccc ggtgccgtgc gcggaagctg ctccaccagc  1200
tccggtgtcc ctgctcaggt cgaatctcag tctcccaacg ccaaggtcac cttctccaac  1260
atcaagttcg gacccattgg cagcaccggc aaccctagcg gcgcaaccc tcccggcgga  1320 aaccgcctg gcaccaccac cacccgccgc cagccacta ccactggaag ctctcccgga   1380
cctacccagt ctcactacgg ccagtgcggc ggtattggct acagcggccc cacggtctgc  1440
gccagcggca caacttgcca ggtcctgaac ccttactact ctcagtgcct gtaaagctcc  1500

<210> SEQ ID NO 99
<211> LENGTH: 497
<212> TYPE: PRT
<213> ORGANISM: Trichoderma reesei

<400> SEQUENCE: 99

Gln Ser Ala Cys Thr Leu Gln Ser Glu Thr His Pro Pro Leu Thr Trp
1               5                   10                  15

-continued

```
Gln Lys Cys Ser Ser Gly Gly Thr Cys Thr Gln Gln Thr Gly Ser Val
                 20                  25                  30
Val Ile Asp Ala Asn Trp Arg Trp Thr His Ala Thr Asn Ser Ser Thr
             35                  40                  45
Asn Cys Tyr Asp Gly Asn Thr Trp Ser Ser Thr Leu Cys Pro Asp Asn
         50                  55                  60
Glu Thr Cys Ala Lys Asn Cys Cys Leu Asp Gly Ala Ala Tyr Ala Ser
 65                  70                  75                  80
Thr Tyr Gly Val Thr Thr Ser Gly Asn Ser Leu Ser Ile Gly Phe Val
                 85                  90                  95
Thr Gln Ser Ala Gln Lys Asn Val Gly Ala Arg Leu Tyr Leu Met Ala
             100                 105                 110
Ser Asp Thr Thr Tyr Gln Glu Phe Thr Leu Leu Gly Asn Glu Phe Ser
         115                 120                 125
Phe Asp Val Asp Val Ser Gln Leu Pro Cys Gly Leu Asn Gly Ala Leu
     130                 135                 140
Tyr Phe Val Ser Met Asp Ala Asp Gly Gly Val Ser Lys Tyr Pro Thr
145                 150                 155                 160
Asn Thr Ala Gly Ala Lys Tyr Gly Thr Gly Tyr Cys Asp Ser Gln Cys
                 165                 170                 175
Pro Arg Asp Leu Lys Phe Ile Asn Gly Gln Ala Asn Val Glu Gly Trp
             180                 185                 190
Glu Pro Ser Ser Asn Asn Ala Asn Thr Gly Ile Gly Gly His Gly Ser
         195                 200                 205
Cys Cys Ser Glu Met Asp Ile Trp Glu Ala Asn Ser Ile Ser Glu Ala
     210                 215                 220
Leu Thr Pro His Pro Cys Thr Thr Val Gly Gln Glu Ile Cys Glu Gly
225                 230                 235                 240
Asp Gly Cys Gly Gly Thr Tyr Ser Asp Asn Arg Tyr Gly Gly Thr Cys
                 245                 250                 255
Asp Pro Asp Gly Cys Asp Trp Asn Pro Tyr Arg Leu Gly Asn Thr Ser
             260                 265                 270
Phe Tyr Gly Pro Gly Ser Ser Phe Thr Leu Asp Thr Thr Lys Lys Leu
         275                 280                 285
Thr Val Val Thr Gln Phe Glu Thr Ser Gly Ala Ile Asn Arg Tyr Tyr
     290                 295                 300
Val Gln Asn Gly Val Thr Phe Gln Gln Pro Asn Ala Glu Leu Gly Ser
305                 310                 315                 320
Tyr Ser Gly Asn Glu Leu Asn Asp Asp Tyr Cys Thr Ala Glu Glu Ala
                 325                 330                 335
Glu Phe Gly Gly Ser Ser Phe Ser Asp Lys Gly Gly Leu Thr Gln Phe
             340                 345                 350
Lys Lys Ala Thr Ser Gly Gly Met Val Leu Val Met Ser Leu Trp Asp
         355                 360                 365
Asp Tyr Tyr Ala Asn Met Leu Trp Leu Asp Ser Thr Tyr Pro Thr Asn
     370                 375                 380
Glu Thr Ser Ser Thr Pro Gly Ala Val Arg Gly Ser Cys Ser Thr Ser
385                 390                 395                 400
Ser Gly Val Pro Ala Gln Val Glu Ser Gln Ser Pro Asn Ala Lys Val
                 405                 410                 415
Thr Phe Ser Asn Ile Lys Phe Gly Pro Ile Gly Ser Thr Gly Asn Pro
             420                 425                 430
```

-continued

```
Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu
```

CELLOBIOHYDROLASE I GENE AND IMPROVED VARIANTS

The United States Government has rights in this invention under contract number DE-AC36-99GO-10337 between the United States Department of Energy and the National Renewable Energy Laboratory, a division of the Midwest Research Institute.

The present application claims priority to PCT Application PCT/US00/19007 filed Jul. 13, 2000, which is hereby incorporated by reference. PCT/US00/19007 claims priority to U.S. Provisional Application 60/143,711 filed Jul. 14, 1999.

FIELD OF THE INVENTION

This invention relates to 1,4-β-cellobiohydrolases or exoglucanases. More specifically, it relates to the *Trichoderma reesei* cellobiohydrolase I gene, the creation of reduced glycosylation variants of the expressed CBH I protein to enable the expression of active enzyme in heterologous hosts, and to the creation of new thermal stabile variants of the enzyme that instill higher thermal tolerance on the protein and improved performance.

BACKGROUND OF THE INVENTION

The surface chemistry of acid pretreated-biomass, used in ethanol production, is different from that found in plant tissues, naturally digested by fungal cellulase enzymes, in two important ways: (1) pretreatment heats the substrate past the phase-transition temperature of lignin; and (2) pretreated biomass contains less acetylated hemicellulose. Thus, it is believed, that the cellulose fibers of pretreated-biomass are coated with displaced and modified lignin. This alteration results in a non-specific binding of the protein with the biomass, which impedes enzymatic activity. Moreover, where the pretreated biomass is a hardwood-pulp it contains a weak net-negatively charged surface, which is not observed in native wood. Therefore, for the efficient production of ethanol from a pretreated biomass such as corn stover, wood or other biomass it is desirable to enhance the catalytic activity of glycosyl hydrolases specifically the cellobiohydrolases.

*Trichoderma reesei* CBH I (SEQ ID NO: 5) is a mesophilic cellulase which plays a major role in the hydrolysis of cellulose. An artificial ternary cellulase system consisting of a 90:10:2 mixture of *T. reesei* CBH I, *Acidothermus cellulolyticus* EI, and *Aspergillus niger* β-D-glucosidase is capable of releasing as much reducing sugar from pretreated yellow poplar as the native *T. reesei* system after 120 h. This result is encouraging for the ultimate success of engineered cellulase systems, because this artificial enzyme system was tested at 50° C., a temperature far below that considered optimal for EI, in order to spare the more heat labile enzymes CBH I and β-D-glucosidase. To increase the efficiency of such artificial enzyme systems it is desirable to engineer new *T. ressei* CBH I variant enzymes capable of active expression in heterologous hosts. The use of the heterologous host *Aspergillus awamori*, could provide an excellent capacity for synthesis and secretion of *T. reesei* CBH I because of its ability to correctly fold and post-translationally modify proteins of eukaryotic origin. Moreover, *A. awamori* is believed to be an excellent test-bed for *Trichoderma* coding sequences and resolves some of the problems associated with site directed mutagenesis and genetic engineering in *Trichoderma*.

In consideration of the foregoing, it is therefore desirable to provide variant cellulase enzymes having enzymatic activity when expressed in a heterologous host, and to provide variant cellulase enzymes that have improve thermal tolerance over the native as produced by *Trichoderma reesei*.

SUMMARY OF THE INVENTION

It is a general object of the present invention to provide variant cellulase enzymes having enzymatic activity when expressed in a heterologous host, such as a filamentous fungi or yeast.

Another object of the invention is to provide a variant exoglucanases characterized by a reduction in glycosylation when expressed in a heterologous host.

Another object of the invention is to provide an active cellobiohydrolase enzyme capable of expression in heterologous fungi including yeast.

Another object of the invention is to provide improved thermal tolerant variants of the cellobiohydrolase enzyme capable of functioning at increased process temperatures.

It is yet another object of the invention to provide a method for reducing the glycosylation of a cellobiohydrolase enzyme for expression in a heterologous host.

The foregoing specific objects and advantages of the invention are illustrative of those which can be achieved by the present invention and are not intended to be exhaustive or limiting of the possible advantages which can be realized. Thus, those and other objects and advantages of the invention will be apparent from the description herein or can be learned from practicing the invention, both as embodied herein or as modified in view of any variations which may be apparent to those skilled in the art.

Briefly, the invention provides a method for making an active cellobiohydrolase in a heterologous host, the method comprising reducing glycosylation of the cellobiohydrolase, reducing glycosylation further comprising reducing an N-glycosylation site amino acid residue with a non-glycosyl accepting amino acid residue. The invention further provides a cellobiohydrolase, comprising the reduced glycosylation variant cellobiose enzymes CBHI-N45A; CBHI-N270A; or CBHI-N384A, or any combination thereof.

DETAILED DESCRIPTION OF THE INVENTION

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The terms "native" and "wild-type" are used interchangeably throughout this disclosure to indicate the origin of the molecule as it occurs in nature.

A method for reducing the glycosylation of an expressed *Trichoderma reesei* CBHI protein by site-directed mutagenesis ("SDM") is disclosed. The method includes replacing an N-glycosylation site amino acid residue, such as asparagines 45, 270, and/or 384 (referenced herein as CBHI-N45A, CBHI-N270A and CBHI-N384A, respectively), with a non-glycosyl accepting amino acid residue, such as is alanine. Various mutagenesis kits for SDM are available to those skilled in the art and the methods for SDM are well known. The description below discloses a procedure for making and using CBHI variants: CBHI-N45A (SEQ ID NO: 6); CBHI-N270A (SEQ ID NO: 7); and CBHI-N384A (SEQ ID NO: 8). The examples below demonstrate the expression of active CBHI in the heterologous fungus *Aspergillus awaniori*.

Variants of CBH I embodiments include mutations that provide for improved end product inhibition and for thermal tolerance.

BRIEF DESCRIPTION OF THE FIGURES

FIG. 1. Coding sequence of the cbh 1 gene (SEQ ID NO: 4). Lower case letters represent the signal sequence, upper case letters the catalytic domain, bolded italics the linker region, and upper case underlined the cellulose-binding domain.

FIG. 2. SDS-PAGE Western blot with anti-CBH I antibody showing the reduction on molecular weight of rCBH I expression clones as a function of introduction of N to A modifications.

EXAMPLE 1

Figure 3:
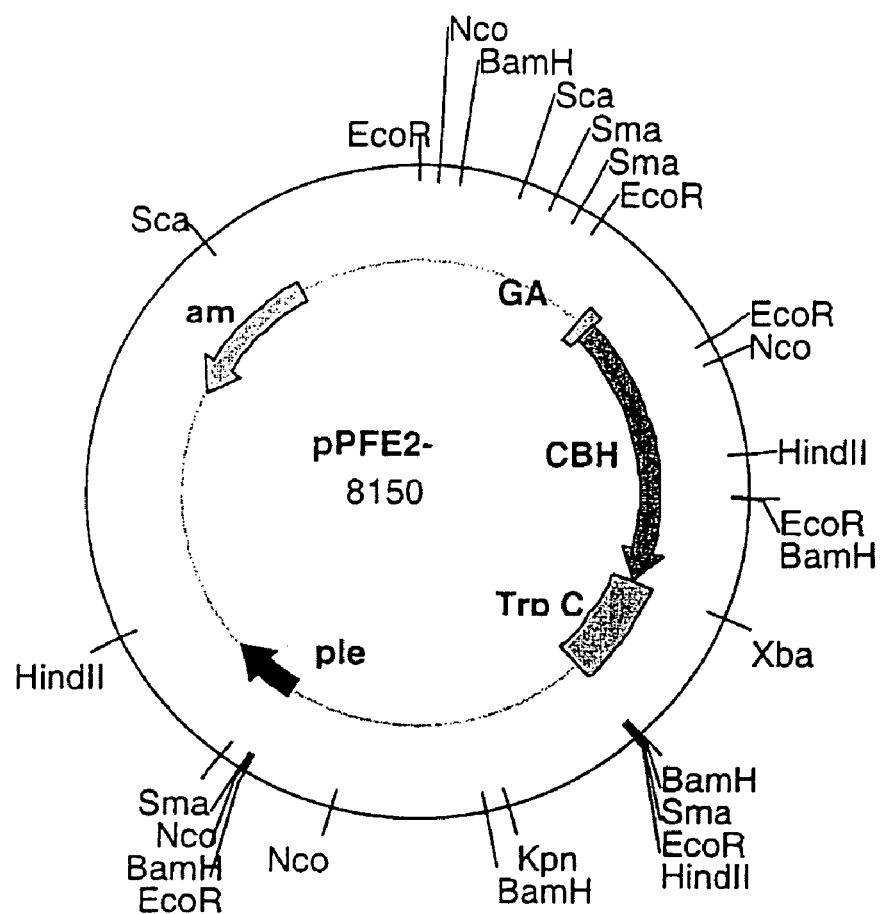
FIG. 3. Plasmid map for the fungal expression vector pPFE2/CBH I.

Acquisition of the CBH I Encoding Sequence

Acquisition of the gene was done by either cDNA cloning or by PCR of the gene from genomic DNA. CBH I cDNA was isolated from a *T. reesei* strain RUT C-30 cDNA library constructed using a PCR-generated probe based on published CBH I gene sequences (Shoemaker, et al., 1983). The cDNA's were cloned (using the Zap Express cDNA kit from Stratagene; cat. #200403) into the XhoI and EcoRI site(s) of the supplied, pre-cut lambda arms. An XhoI site was added to the 3' end of the cDNA during cDNA synthesis, and sticky-ended RE linkers were added to both ends. After XhoI digestion, one end has an XhoI overhang, and the other (5' end) has an Eco RI overhang. The insert can be removed from this clone as an approximately 1.7 kb fragment using SalI or SpeI plus XhoI in a double digest. There are two Eco RI, one Bam HI, 3 SacI and one HindIII sites in the coding sequence of the cDNA itself. The plasmid corresponding to this clone was excised in vivo from the original lambda clone, and corresponds to pB210-5A. Thus, the cDNA is inserted in parallel with a Lac promoter in the pBK-CMV parent vector. Strain pB210-5A grows on LB+kanamycin (50 μg/mL).

Acquisition of the cbh I gene was also achieved by PCR of genomic DNA. With this approach the fungal chromosomal DNA from *T. reesei* strain Rut C-30 was prepared by grinding the fungal hypae in liquid nitrogen using a mortar and pestle to a fine powder. The genomic DNA was then extracted from the cell debris using a Qiagen DNAeasy Plant Mini kit. Amplification of the DNA fragment that encodes for the cbh I gene, including introns, was performed using polymerase chain reaction (PCR) with specific primers for the *T. reesei* cbh I gene. The primers 5'-AGAGAGTCTA-GACACGGAGCTTACAGGC-3' (SEQ ID NO: 9) that introduces a Xba I site and the primer 5'-AAA-GAAGCGCGGCCGCGCCTGCACTCTCCAATCGG-3' (SEQ ID NO: 97) that introduces a unique Not I site were used to allowing cloning into the pPFE *Aspergillus/E. coli* shuttle vectors that are described below. The amplified PCR product was then gel purified and cloned directly into the vectors.

EXAMPLE 2

Production of Active Recombinant CBH I (rCBH I) in *Aspergillus awamori*. Construction of the Fungal Expression Vectors pPFE-1/CBH I and pPFE-2/CBH I The coding sequence for *T. reesei* CBH I was successfully inserted and expressed in *Aspergillus awamori* using the fungal expression vector pPFE2 (and pPFE1). Vectors pPFE1 and pPFE2 are *E. coli-Aspergillus* shuttle vectors, and contain elements required for maintenance in both hosts. Both pPFE-1 and pPFE-2 vectors direct the expression of a fusion protein with a portion of the glucoamylase gene fused to the gene of interest. The pPFE1 vector contains a region of the glucoamylase gene, with expression under the control of the *A. awamori* glucoamylase promoter. The protein of interest is expressed as a fusion protein with the secretion signal peptide and 498 amino acids of the catalytic domain of the glucoamylase protein. The majority of the work presented here was done using the pPFE2 expression vector, which was chosen because of its smaller size, simplifying the PCR mutation strategy by reducing extension time.

The major features of the pPFE2-CBH1 construct are shown in FIG. 3. With both the pPFE1/CBH1 and the pPFE2/CBH1 vectors, the sequence immediately upstream of the Not I site encodes a LysArg dipeptide. A host KEX-2 like protease recognizes this dipeptide sequence during the secretion process, and the fusion peptide is cleaved, removing the glucoamylase secretion signal peptide or the longer catalytic domain of glucoamylase in the case of pPFE1. In this way, the recombinant CBH I protein experiences an "efficient ride" through the *A. awamori* secretion system and is expressed with the native N-terminal protein. The net result is that the recombinant CBH I is processed so that it can accumulate in the medium without its glucoamylase secretion signal fusion partner. The vector contains the *Streptoalloteichus hindustanus* phleomycin resistance gene, under the control of the *A. niger* β-tubulin promoter, for positive selection of *Aspergillus* transformants. The pPFE/CBH1 vector also contains a lactamase gene for positive selection using ampilcillin in *E. coli*, and also contains the *A. niger* trpC terminator. The insertion of the CBH I coding sequence into the pPFE vectors was accomplished using two methods. Vector DNA was first produced in 500 mL cultures of *E. coli* XL1 Blue and the plasmids purified using Promega maxi-preps DNA purification kits.

Approach 1: Blunt-Xba I Fragment Generation.
1. Oligonucleotides were designed to give a blunt end on the 5' end and an engineered Xba I site on the 3' end of the PCR fragment.
2. The full-length coding sequence for CBH I was obtained by PCR using Pfu DNA polymerase and using the cDNA construct pB510-2a as the template. Pfu DNA polymerase generates blunt-ended PCR products exclusively.
3. The pPFE vectors were digested using NotI and confirmed by agarose gel electrophoresis. The NotI overhang was then digested using Mung Bean nuclease. The DNA was purified and the vector and CBH I PCR fragment digested using XbaI.
4. The vector and PCR product were then ligated using T4 DNA ligase and the DNA used to transform *E. coli* XL-1 Blue and *E. coli* DH5α using electroporation.

Approach 2: NotI-XbaI Fragment Approach.
1. Oligonucleotides were designed to give a Not 1 site on the 5' end, and an engineered Xba I site on the 3' end of the PCR fragment.
2. The full-length coding sequence for CBH I was obtained by PCR using Pfu DNA polymerase and using the cDNA construct pB510-2a as the template.
3. The pPFE vectors and the PCR product were digested using Not 1 and Xba 1
4. The CBH I PCR product was directionally cloned into the pPFE2 vector using T4 DNA ligase and transformed into *E. coli* XL-1 Blue.
5. The insertion of the CBH I coding sequence into the pPFE2 vector was confirmed using PCR, restriction digest analysis, and DNA sequencing through the insertion sites. The entire coding sequence of the insert was also confirmed by DNA sequencing.

The constructs produced using these two methods was then used to transform *A. awamori* and to express rCBH I, as confirmed by western blot analysis of culture supernatant. The rCBH I expressed in *A. awamori* tends to be over glycosylated as evidenced by the higher molecular weight observed on western blot analysis. Over glycosylation of CBH I by *A. awamori* was confirmed by digestion of the recombinant protein with endoglycosidases. Following endoglycosidase H and F digestion, the higher molecular weight form of the protein collapses to a molecular weight similar to native CBH I.

EXAMPLE 3

Method for Producing PCR Site Directed Mutations for Glycosylation Removal and Improved Thermalstability The QuickChange™ Site Directed Mutagenesis kit (StrataGene, San Diego, Calif.) was used to generate mutants with targeted amino acid substitutions. To introduce these specific amino acid substitutions, mutagenic primers (between 25 and 45 bases in length) were designed to contain the desired mutation that would result in the targeted amino acid substitution. Pfu DNA polymerase was then used to amplify both strands of the double-stranded vector, which contained the CBH I insertion sequence, with the resultant inclusion of the desired mutation from the synthetic oligonucleotides. Following temperature cycling, the product was treated with the exonuclease Dpn I to digest the parental methylated DNA template and the PCR product was used to transform Epicurian Coli XL1-Blue supercompetent cells.

The vector pPFE2/CBHI requires a relatively long PCR reaction (8.2 kB) to make site-specific changes using the Stratagene Quik Change protocol. The PCR reaction was optimized as follows using a GeneAmp PCR System 2400, Perkin Elmer Corporation. The reaction mixture contained 50 ng of template DNA, 125 ng each of the sense and antisense mutagenic primers, 5 mL of Stratagene 10× cloned Pfu buffer, 200 µM of each: dNTP, 5 mM $MgCl_2$ (total final concentration of $MgCl_2$ is 7 mM); and 2.5 U Pfu Turbo DNA polymerase. The PCR reaction was carried out for 30 cycles, each consisting of one minute denaturation at 96° C., 1 minute annealing at 69° C. and a final extension for 10 min at 75° C., followed by a hold at 4° C. Agarose gel electrophoresis, ethidium bromide staining, and visualization under UV transillumination were used to confirm the presence of a PCR product.

PCR products were digested with the restriction enzyme Dpn1, to degrade un-mutagenized parental DNA, and transformed into *E. coli* (Stratagene Epicurian Coli Supercompetent XL-1 Cells). Ampicillin resistant colonies were picked from LB-amp100 plates and mutations were confirmed by DNA sequencing.

Template DNA from *E. coli* XL1-blue cells transformed with Dpn1 treated mutaginzed DNA was prepared for sequencing using the QIAprep-spin plasmid purification mini-prep procedure (Qiagen, Inc.). The transformed XL1-blue cells where grown overnight in 5 mL of LB broth with 100 µg/mL ampicillin selection. Cells were removed by centrifugation and the plasmid isolated using the protocol outlined in the QIAprep-spin handbook. The concentration of the template DNA was adjusted to 0.25 µg/µL and shipped along with sequencing oligonucleotides to the DNA Sequencing Facility at Iowa State University.

After the mutation was confirmed by DNA sequence alignment comparisons using the software package OMIGA, and the DNA was prepared for transformation of *A. awamori*. The transformed *E. coli* XL1/blue cells were grown overnight on LB plates with 100 µg/mL ampicillin at 37° C. A single colony was then used to inoculate a 1 L baffled Erlenmeyer flask that contained 500 mL of LB broth and 100 µg/mL ampicillin. The culture was allowed to grow for 16 to 20 hours at 37° C. with 250 rpm shaking in a NBS reciprocating shaking incubator. The cells were harvested and the plasmid DNA purified using a Promega maxi-prep purification kit. The purified maxi-prep DNA was subsequently used to transform *A. awamori* spheroplasts using the method described below.

Transformation of *Aspergillus awamori* with *Trichoderma reesei* CBH I Coding Sequence. Generating Fungal Spheroplasts.

*A. awamori* spheroplasts were generated from two-day-old cultures of mycelia pellets. A heavy spore suspension was inoculated into 50 mL of CM broth (5.0 g/L yeast extract; 5.0 g/L tryptone; 10 g/L glucose; 50 mL/L 20× Clutterbuck's salts, pH 7.5 (adjusted by addition of 2.0N NaOH)) and grown at 225 rpm and 28° C. in a baffled 250 mL Erlenmeyer flask. The mycelia were collected by filtration through Miracloth and washed with ~200 mL KCM (0.7M KCl; 10 mM MOPS pH 5.8). The washed mycelia were transferred to 50 mL, of KCM+500 mg Novazym 234 in a 50-mL unbaffled flask and incubated O/N at 80 rpm and 30° C. After digestion, the remaining mycelia was removed by filtration through Miracloth and the spheroplasts were collected in 50 mL disposable tubes and pelleted at 2500×g in a swinging bucket rotor for 15 minutes. The supernatant was discarded and the spheroplasts gently resuspended in 20 mL 0.7M KCl by tituration with a 25-mL disposable pipet. The spheroplasts were pelleted and washed again, then resuspended in 10 mL KC (0.7M KCl+50 mM $CaCl_2$). After being pelleted, the spheroplasts were resuspended into 1.0 mL of KC.

Transformation was carried out using 50 µL of spheroplasts+5 µL DNA (pPFE1 or pPFE2 ~200 µg/mL)+12.5 µL PCM (40% PEG8000+50 mM CaCl2+10 mM MOPS pH 5.8). After incubation for 60 mins on ice, 0.5 mL PCM was added and the mixture was incubated for 45 mins at room temperature. One milliliter of KCl was added and 370 µL of the mix was added to 10 mL of molten CMK (CM+2% agar+0.7M KCl) top agar at 55° C. This mixture was immediately poured onto a 15 mL CM170 plate (CM+2% agar+170 µg/mL Zeocin). Negative transformation controls substituted sterile $dH_2O$ for DNA. Plating the transformation mix onto CM plates without Zeocin performed positive spheroplast regeneration controls. The poured plates were incubated at 28° C. in the dark for 2-7 days.

Transformation of *Aspergillus awamori* with Native and Modified CBH I Coding Sequence.

*Aspergillus awamori* spore stocks were stored at −70° C. in 20% glycerol, 10% lactose. After thawing, 200 µL of spores were inoculated into 50 mL CM broth in each of eight-baffled 250 mL Erlenmeyer flask. The cultures were grown at 28° C., 225 rpm for 48 h. The mycelial balls were removed by filtration with sterile Miracloth (Calbiochem, San Diego, Calif.) and washed thoroughly with sterile KCM. Approximately 10 g of washed mycelia were transferred to 50 mL KCM+250 mg Novozym234 in a 250 mL baffled Erlenmeyer flask. The digestion mixture was incubated at 30° C., 80 rpm for 1-2 h and filtered through Miracloth into 50 mL conical centrifuge tubes. The spheroplasts were pelleted at 2000×g for 15 min and resuspended in 0.7M KCl by gentle tituration with a 25 mL pipette. This was repeated once. After a third pelleting, the spheroplasts were resuspended in 10 mL KC, pelleted and resuspended in 0.5 mL KC using a wide-bore pipet tip. The washed spheroplasts were transformed by adding 12.5 µL PCM and 5 µL DNA (~0.5 µg/µL) to 50 µL of spheroplasts in sterile 1.5 mL Eppendorf tubes. After incubation on ice for 45 minutes, 0.5 mL of room temperature PCM was added to the transformation mixture and was mixed by tituration with a wide bore pipet tip. The mixture was incubated at room temperature for 45 minutes. One milliliter of KC was added and mixed. The mixture was allocated between four tubes of CM top agar at 55° C., which were each poured over a 15 mL CM170 plate. The plates were incubated at 28° C. for 2-3 days. Subsurface colonies were partially picked with a sterile wide bore pipet tip, exposing the remaining part of the colony to air and promoting rapid sporulation. After sporulation, spores were streaked onto several successive CM10 or CM300 plates. After a monoculture was established, heavily sporulated plates were flooded with sterile spore suspension medium (20% glycerol, 10% lactose), the spores were suspended and aliquots were frozen at −70° C. Working spore stocks were stored on CM slants in screw cap tubes at 4° C. Protein production was confirmed and followed by western blot using anti-CBH I monoclonal antibodies and the Novex Western Breeze anti-mouse chromogenic detection kit (Novex, San Diego, Calif.). Extracting genomic DNA using the YeaStar Genomic DNA Kit (Zymo Research, Orange, Calif.) and carrying out PCR with pfu-turbo DNA polymerase (Stratagene, La Jolla) and cbh 1 primers confirmed insertion of the gene.

Production and Purification of Native rCBH I Enzyme from *Aspergillus awamori*.

For enzyme production, spores were inoculated into 50 mL CM basal starch medium, pH 7.0, and grown at 32° C., 225 rpm in 250 mL baffled flasks. The cultures were transferred to 1.0 L of basal starch medium in 2800 mL Fernbach flasks and grown under similar conditions. For large-scale enzyme production (>1 mg), these cultures were transferred to 10 L basal starch medium in a New Brunswick BioFlo3000 fermenter (10-L working volume) maintained at 20% DO, pH 7.0, 25° C., and 300 rpm. The fermentation was harvested by filtration through Miracloth after 2-3 days of growth.

After further clarification by glass fiber filtration, the rCBH I protein was purified by passing the fermentation broth over four CBinD900 cartridge columns (Novagen, Madison, Wis.) connected in parallel using a Pharmacia FPLC System loading at 1.0 mL/min (Amersham Pharmacia Biotech, Inc., Piscataway, N.J.). The cartridges were equilibrated in 20 mM Bis-Tris pH 6.5 prior to loading and washed with the same buffer after loading. The bound rCBH I was then eluted with 100% ethylene glycol (3 mL/column) using a syringe. Alternatively, the supernatant was passed over a para-aminophenyl β-D-cellobioside affinity column, washed with 100 mM acetate buffer, pH 5.0, 1 mM gluconolactone and eluted in the same buffer containing 10 mM cellobiose. In either method, the eluted rCBH I was concentrated in Millipore Ultrafree-15 spin concentrator with a 10 kDa Biomax membrane to <2.0 mL and loaded onto a Pharmacia SuperDex200 16/60 size-exclusion column. The mobile phase was 20 mM sodium acetate, 100 mM sodium chloride, and 0.02% sodium azide, pH 5.0 running at 1.0 mL/min. The eluted protein was concentrated and stored at 4° C. Protein concentrations were determined for each mutant based upon absorbance at 280 nm and calculated from the extinction coefficient and molecular weight for each individual protein as determined by primary amino acid sequence using the ProtParam tool on the ExPASy website (http://www.expasy.ch/tools/protparam.html).

| Clutterbuck's Salts (20X) | |
|---|---|
| Na$_2$NO$_3$ | 120.0 g |
| KCl | 10.4 |
| MgSO$_4$•7H$_2$O | 10.4 |
| KH$_2$PO$_4$ | 30.4 |
| CM- | |
| Yeast Extract- | 5 g/L |
| Tryptone- | 5 g/L |
| Glucose- | 10 g/L |
| Clutterbuck's Salts- | 50 mL |

Add above to 900 mL dH$_2$O, pH to 7.5, bring to 1000 mL
CM Agar—CM+20 g/L Agar
CMK—CM Agar+0.7M KCl
CM100—CM+100 µg/mL Zeocin (Invitrogen, Carlsbad, Calif.)
CM170—CM+170 µg/mL Zeocin, 15 mL/plate
KCl—0.7M KCl
KC—0.7M KCl+50 mM CaCl$_2$
KCM—0.7M KCl+10 mM MOPS, pH 5.8
PCM—40% PEG 8000, 50 mM CaCl$_2$, 10 mM MOPS pH 5.8 (mix 4 mL 50% PEG+0.5 mL 500 mM CaCl$_2$ stock+ 0.5 mL 100 mM MOPS stock)

| Basal Starch Medium- | |
|---|---|
| Casein Hydrolysate, Enzymatic | 5 g/L |
| NH$_4$CL | 5 g/L |
| Yeast Extract | 10 g/L |
| Tryptone | 10 g/L |
| MgSO$_4$*7H$_2$O | 2 g/L |
| Soluble Starch | 50 g/L |
| Buffer (Bis-Tris-Propane) | 50 mM |
| pH to 7.0 with NaOH | |

EXAMPLE 4

Production of Reduced Glycosylation rCBH I: Sites N270A; N45A; and N384A rCHI/pPFE2 has been optimized using site-directed mutagenesis to achieve expression of native molecular weight CBH I in *A. awamori* by the following ways. The QuickChange SDM kit (Stratagene, San Diego, Calif.) was used to make point mutations, switch amino acids, and delete or insert amino acids in the native cbh 1 gene sequence. The Quick Change SDM technique was performed using thermotolerant Pfu DNA polymerase, which replicates both plasmid strands with high fidelity and without displacing the mutant oligonucleotide primers. The procedure used the polymerase chain reaction (PCR) to modify the cloned cbh 1 DNA. The basic procedure used a supercoiled double stranded DNA (dsDNA) vector, with the cbh 1 gene insert, and two synthetic oligonucleotide primers containing a desired mutation. The oligonucleotide primers, each complimentary to opposite strands of the vector, extend during temperature cycling by means of the polymerase. On incorporation of the primers, a mutated plasmid containing the desired nucleotide substitutions was generated. Following temperature cycling, the PCR product was treated with a Dpn1 restriction enzyme. Dpn1 is specific for methylated and hemi-methylated DNA and thus digests the unmutated parental DNA template, selecting for the mutation-containing, newly synthesized DNA. The nicked vector DNA, containing the desired mutations, was then transformed into *E. coli*. The small amount of template DNA required to perform this reaction, and the high fidelity of the Pfu DNA polymerase contribute to the high mutation efficiency and minimizes the potential for the introduction of random mutations. Three glycosylation-site amino acids on the pro surface were targeted for substitution of an alanine (A) residue in place of asparagines (N). Single site substitutions were successfully completed in the cbh 1 coding sequence at sites N45, N270, and N384, of Seq. ID NO: 4 by site-directed mutagenisis, and confirmed by DNA sequencing.

Double and triple combinations of this substitution have also been completed in the cbh 1 coding sequence at sites N45, N270, and N384 by site directed mutagenisis and confirmed by DNA sequencing. These double and triple site constructs also yield rCBH I enzymes with reduced glycosylation and, presumably, native activity.

variants CBHIN45A and CBHI384A also demonstrate a reduction in amount of glycosylation and native activity when expressed from the heterologous host *A. awamori* and when combined in the double mutations CBHIN270/45A and CBHIN270/384A reduce the level of glycosylation further.

EXAMPLE 5

Amino Acid Mutations Targeted to Improve Thermal Tolerance of CBH I *Helix* Capping Mutants All α-helices display dipole moments, i.e. positive at N-terminal and negative at C-terminal. Compensation for such dipole moments (capping) has been observed in a number of protein structures[1,2] and has been shown to improve the protein stability. For example, the introduction of a negatively charged amino acid at the N-terminus and a positively charged amino acid at C-terminus of an α-helix increased the thermostability of T4 lysozyme[3] and hen lysozyme[4], via an electrostatic interaction with the "helix dipole." Five amino acid sites were identified for helix capping (see Table 5).

Peptide Strain Removal Mutants.

A small fraction of residues adopt torsion angles, phi-psi angles, which are unfavorable. It has been shown that mutation of such residues to Gly increased the protein stability as much as 4 kcal/mol. One amino acid site was selected for peptide strain removal (see Table 3).

*Helix* Propensity Mutants.

Two amino acid sites were selected for helix propensity improvement.

Disulfide Bridge Mutants.

Disulfide bonds introduced between amino acid positions 9 and 164 and between 21 and 142 in phage T4 lysozyme have been shown to significantly increase the stability of the

TABLE 1

| Construct | Host | MW (kDa) | $K_m$ μmol pNPL | Vmax μmol pNP/min/mg protein |
|---|---|---|---|---|
| *T. reesei* | None | 57.8 | 1.94 | 0.746 |
| rCBHI wt cDNA | *A. awamori* | 63.3 | 2.14 | 0.668 |
| rCBHI wt genomic | *A. awamori* | 63.3 | — | — |
| rCBHI N270A | *A. awamori* | 61.7 | 2.25 | 0.489 |
| rCBHI N384A | *A. awamori* | 61.3 | — | — |
| rCBHI wt genomic (G) | *A. awamori* | 63.3 | — | — |
| rCBHI N45A | *A. awamori* | 58.3 | — | — |
| rCBHI N270/45A | *A. awamori* | 58.3 | — | — |
| rCBHI N384/270A | *A. awamori* | 58.8 | | |

As shown in Table 1, Western blot analysis of the supernatant, obtained from a single glycosylaition site mutant CBHIN270A culture expressed in *A. awamori*, demonstrated that a decrease, to lower molecular weight (61.7 kDa), in the amount of glycosylation of the protein had occurred, as compared to that in the wild type cDNA (63.3 kDa), and the wild type genomic DNA (63.3 kDa). These results demonstrate a reduction in the level of glycosylation in the reduced glycosylation mutant CBHIN270A, via expression in *A. awamori*. It is also shown, in the Table, that the CBHIN270A enzyme nearly retained its native enzymatic activity when assayed using the pNPL substrate. The respective enzymes toward thermal denaturation. The engineered disulfide bridge between residues 197 and 370 of CBH I should span the active site cleft and enhance its thermostability. The active site of CBH I is in a tunnel. The roof over the tunnel appears to be fairly mobile (high temperature-factors). At an elevated temperature the mobility of the tunnel is too significant to position all the active site residues. The disulfide linkage should stabilize the roof of the tunnel making the enzyme a consistent exocellulase even at a high temperature. Two amino acid sites were identified for new disulfide bridge generation.

Deletion Mutants.

Thermostable proteins have shorter loops that connect their structural elements than typical proteins. Our sequence alignment of CBH I, with its close homologs, suggests that the following residues may be deleted without significantly affecting its function. These loops exhibited high mobility as well. Three loops were identified, but these modifications were considered high risk (buried hydrophobic regions may be exposed to solvent upon deletion of a natural loop) and will be saved for future work.

Proline Replacement Mutants.

The unique structure of proline dictates that fewer degrees of freedom are allowed around the alpha carbon that most other amino acids. The result of this structure is that peptides tend to loose flexibility in regions rich with proline. In order to assess possible sites for replacement of existing amino acids with proline, the phi/psi angles of candidate amino acid sites must conform with those consistent with proline. Each new site must also be evaluated for allowable side chain interactions and assurance that interactions with substrate are not altered. Seventeen amino acid sites were identified for proline replacement (See Table 2).

EXAMPLE 6

Nucleic Acid Sequence of a Variant Exoglucance

Figure 4:
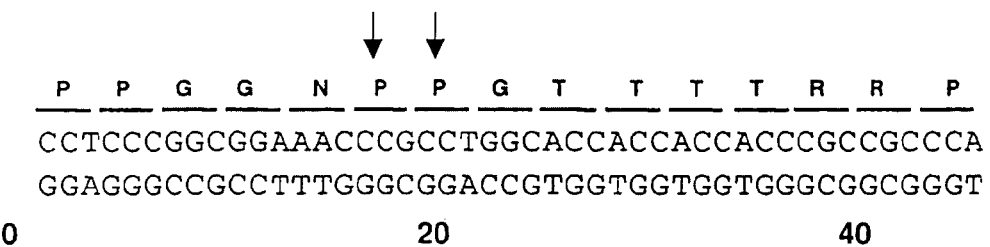
FIG. 4. Coding sequence, SEQ ID NO: 19, for the linker region of the cbh1 gene, SEQ ID NO: 4, showing additional proline nucleotides that effect conformation of the linker region in the protein structure.

The present example demonstrates the utility of the present invention for providing a nucleic acid molecule having a nucleic acid sequence that has a sequence 5'-GGCGGAAAC<u>CCGCCT</u>GGCACCACC-3' (SEQ ID NO: 3). The identified nucleic acid sequence presents a novel linker region nucleic acid sequence that differs from previously reported nucleic acid sequence by the addition of one codon, and the alteration of an adjacent codon, both encoding a proline (See FIG. 4). The invention in some aspects thus provides a nucleic acid molecule encoding a cellobiohydrolase that comprises a linker region of about 6 to 20 amino acids in length as identified here.

TABLE 2

Proline mutations to improve thermal tolerance.

| Mutation | Native sequence and mutatgenic oligo-nucleotide |
|---|---|
| SEQ ID NO: 10<br>S8P-native sense strand | 5'-GCACTCTCCAATCGGAGACTCACCCG-3' |
| SEQ ID NO: 11<br>Mutagenic sense strand | 5'-GCACTCTCCAACCGGAGACTCACCCG-3' |
| SEQ ID NO: 12<br>Mutagenic anti-sense strand | 5'-CGGGTGAGTCTCCGGTTGGAGAGTGC-3' |
| SEQ ID NO: 13<br>N27P-native sense strand | 5'-GGCACGTGCACTCAACAGACAGGCTCCG-3' |
| SEQ ID NO: 14<br>Mutagenic sense strand | 5'-GGCACGTGCACTCCACAGACAGGCTCCG-3' |
| SEQ ID NO: 15<br>Mutagenic anti-sense strand | 5'-CGGAGCCTGTCTGTGGAGTGCACGTGCC-3' |
| SEQ ID NO: 16<br>A43P-native sense strand | 5'-GGCGCTGGACTCACGCTACGAACAGCAGCACG-3' |
| SEQ ID NO: 17<br>Mutagenic sense strand | 5'-GGCGCTGGACTCACCCTACGAACAGCAGCACG-3' |
| SEQ ID NO: 18<br>Mutagenic anti-sense strand | 5'-CGTGCTGCTGTTCGTAGGGTGAGTCCAGCGCC-3' |
| SEQ ID NO: 19<br>G75P-native sense strand | 5'-GCTGTCTGGACGGTGCCGCCTACGCG-3' |
| SEQ ID NO: 20<br>Mutagenic sense strand | 5'-GCTGTCTGGACCCTGCCGCCTACGCG-3' |
| SEQ ID NO: 21<br>Mutagenic anti-sense strand | 5'-CGCGTAGGCGGCAGGGTCCAGACAGC-3' |
| SEQ ID NO: 22<br>G94P-native sense strand | 5'-GCCTCTCCATTGGCTTTGTCACCC-3' |
| SEQ ID NO: 23<br>Mutagenic sense strand | 5'-GCCTCTCCATTCCCTTTGTCACCC-3' |
| SEQ ID NO: 24<br>Mutagenic anti-sense strand | 5'-GGGTGACAAAGGGAATGGAGAGGC-3' |
| SEQ ID NO: 25<br>E190P-native sense strand | 5'-GGCCAACGTTGAGGGCTGGGAGCC-3' |

TABLE 2-continued

Proline mutations to improve thermal tolerance.

| Mutation | Native sequence and mutatgenic oligo-nucleotide |
|---|---|
| SEQ ID NO: 26<br>Mutagenic sense strand | 5'-GGCCAACGTTCCGGGCTGGGAGCC-3' |
| SEQ ID NO: 27<br>Mutagenic anti-sense strand | 5'-GGCTCCCAGCCCGGAACGTTGGCC-3' |
| SEQ ID NO: 28<br>S195P-native sense strand | 5'-GGCTGGGAGCCGTCATCCAACAACGCG-3' |
| SEQ ID NO: 29<br>Mutagenic sense strand | 5'-GGCTGGGAGCCGCCATCCAACAACGCG-3' |
| SEQ ID NO: 30<br>Mutagenic anti-sense strand | 5'-CGCGTTGTTGGATGGCGGCTCCCAGCC-3' |
| SEQ ID NO: 31<br>K287P-native sense strand | 5'-CGATACCACCAAGAAATTGACCGTTGTCACCC-3' |
| SEQ ID NO: 32<br>Mutagenic sense strand | 5'-CGATACCACCAAGCCATTGACCGTTGTCACCC-3' |
| SEQ ID NO: 33<br>Mutagenic anti-sense strand | 5'-GGGTGACAACGGTCAATGGCTTGGTGGTATCG-3' |
| SEQ ID NO: 34<br>A299P-native sense strand | 5'-CGAGACGTCGGGTGCCATCAACCGATAC-3' |
| SEQ ID NO: 35<br>Mutagenic sense strand | 5'-CGAGACGTCGGGTCCCATCAACCGATAC-3' |
| SEQ ID NO: 36<br>Mutagenic anti-sense strand | 5'-GTATCGGTTGATGGGACCCGACGTCTCG-3' |
| SEQ ID NO: 37<br>Q312P/N315P-native sense strand | 5'-GGCGTCACTTTCCAGCAGCCCAACGCCGAGCTTGG-3' |
| SEQ ID NO: 38<br>Mutagenic sense strand | 5'-GGCGTCACTTTCCCGCAGCCCCCCGCCGAGCTTGG-3' |
| SEQ ID NO: 39<br>Mutagenic anti-sense strand | 5'-CCAAGCTCGGCGGGGGGCTGCGGGAAAGTGACGCC-3' |
| SEQ ID NO: 40<br>G359P-native sense strand | 5'-GGCTACCTCTGGCGGCATGGTTCTGG-3' |
| SEQ ID NO: 41<br>Mutagenic sense strand | 5'-GGCTACCTCTCCCGGCATGGTTCTGG-3' |
| SEQ ID NO: 42<br>Mutagenic anti-sense strand | 5'-CCAGAACCATGCCGGGAGAGGTAGCC-3' |
| SEQ ID NO: 43<br>S398P/S401P-native sense strand | 5'-GCGGAAGCTGCTCCACCAGCTCCGGTGTCCCTGC-3' |
| SEQ ID NO: 44<br>Mutagenic sense strand | 5'-GCGGAAGCTGCCCCACCAGCCCCGGTGTCCCTGC-3' |
| SEQ ID NO: 45<br>Mutagenic anti-sense strand | 5'-GCAGGGACACCGGGGCTGGTGGGGCAGCTTCCGC-3' |
| SEQ ID NO: 46<br>A414P-native sense strand | 5'-GTCTCCCAACGCCAAGGTCACC-3' |
| SEQ ID NO: 47<br>Mutagenie sense strand | 5'-GTCTCCCAACCCCAAGGTCACC-3' |
| SEQ ID NO: 48<br>Mutagenic anti-sense strand | 5'-GGTGACCTTGGGGTTGGGAGAC-3' |
| SEQ ID NO: 49<br>N431P/S433P-native sense strand | 5'-GGCAGCACCGGCAACCCTAGCGGCGGCAACCC-3' |
| SEQ ID NO: 50<br>Mutagenie sense strand | 5'-GGCAGCACCGGCCCCCCTCCCGGCGGCAACCC-3' |

TABLE 2-continued

Proline mutations to improve thermal tolerance.

| Mutation | Native sequence and mutatgenic oligo-nucleotide |
|---|---|
| SEQ ID NO: 51<br>Mutagenic anti-sense strand | 5'-GGGTTGCCGCCGGGAGGGGGGCCGGTGCTGCC-3' |

TABLE 3

Mutation to remove peptide strain.

| Mutation site | Native sequence and mutatgenic oligonucle-otide |
|---|---|
| SEQ ID NO: 52<br>S99G-native sense strand | 5'-GGCTTTGTCACCCAGTCTGCGCAGAAGAACGTTGGC-3' |
| SEQ ID NO: 53<br>Mutagenic sense strand | 5'-GGCTTTGTCACCCAGGGTGCGCAGAAGAACGTTGGC-3' |
| SEQ ID NO: 54<br>Mutagenic anti-sense strand | 5'-GCCAACGTTCTTCTGCGCACCCTGGGTGACAAAGCC-3' |

TABLE 3b

Y245G analogs to remove product inhibition.

| Mutation site | Native sequence and mutatgenic oligo-nucleotide |
|---|---|
| SEQ ID NO: 55<br>R251A-native sense strand | 5'-CCGATAACAGATATGGCGGC-3' |
| SEQ ID NO: 56<br>Mutagenic sense strand | 5'-CCGATAACGCCTATGGCGGC-3' |
| SEQ ID NO: 57<br>Mutagenic anti-sense strand | 5'-GCCGCCATAGGCGTTATCGG-3' |
| SEQ ID NO: 58<br>R394A-native sense strand | 5'-CCCGGTGCCGTGCGCGGAAGCTGCTCCACC-3' |
| SEQ ID NO: 59<br>Mutagenic sense strand | 5'-CCCGGTGCCGTGGCCGGAAGCTGCTCCACC-3' |
| SEQ ID NO: 60<br>Mutagenic anti-sense strand | 5'-GGTGGAGCAGCTTCCGGCCACGGCACCGGG-3' |
| SEQ ID NO: 61<br>F338A-native sense strand | 5'-GCTGAGGAGGCAGAATTCGGCGGATCCTCTTTCTC-3' |
| SEQ ID NO: 62<br>Mutagenic sense strand | 5'-GCTGAGGAGGCAGAAGCCGGCGGATCCTCTTTCTC-3' |
| SEQ ID NO: 63<br>Mutagenic anti-sense strand | 5'-GAGAAAGAGGATCCGCCGGCTTCTGCCTCCTCAGC-3' |
| SEQ ID NO: 64<br>R267A-native sense strand | 5'-GGAACCCATACCGCCTGGGCAACACCAGC-3' |
| SEQ ID NO: 65<br>Mutagenic sense strand | 5'-GGAACCCATACGCCCTGGGCAACACCAGC-3' |
| SEQ ID NO: 66<br>Mutagenic anti-sense strand | 5'-GCTGGTGTTGCCCAGGGCGTATGGGTTCC-3' |
| SEQ ID NO: 67<br>E385A-native sense strand | 5'-CCTACCCGACAAACGAGACCTCCTCCACACCCGG-3' |
| SEQ ID NO: 68<br>Mutagenic sense strand | 5'-CCTACCCGACAAACGCCACCTCCTCCACACCCGG-3' |

TABLE 3b-continued

Y245G analogs to remove product inhibition.

| Mutation site | Native sequence and mutatgenic oligo-nucleotide |
| --- | --- |
| SEQ ID NO: 69<br>Mutagenic anti-sense strand | 5'-CCGGGTGTGGAGGAGGTGGCGTTTGTCGGGTAGG-3' |

TABLE 4

N to A mutations to remove glycosylation.

| Mutant | Native sequence and mutagenic oligonucleotide |
| --- | --- |
| SEQ ID NO: 70<br>N45A-native sense strand | 5'-GGACTCACGCTACGAACAGCAGCACGAACTGC-3' |
| SEQ ID NO: 71<br>Mutagenic sense strand | 5'-GGACTCACGCTACGGCCAGCAGCACGAACTGC-3' |
| SEQ ID NO: 72<br>Mutagenic anti-sense strand | 5'-GCAGTTCGTGCTGCTGGCCGTAGCGTGAGTCC-3' |
| SEQ ID NO: 73<br>N270A-native sense strand | 5'-CCCATACCGCCTGGGCAACACCAGCTTCTACGGCCC-3' |
| SEQ ID NO: 74<br>Mutagenic sense strand | 5'-CCCATACCGCCTGGGCGCCACCAGCTTCTACGGCCC-3' |
| SEQ ID NO: 75<br>Mutagenic anti-sense strand | 5'-GGGCCGTAGAAGCTGGTGGCGCCCAGGCGGTATGGG-3' |
| SEQ ID NO: 76<br>N384A-native sense strand | 5'-GGACTCCACCTACCCGACAAACGAGACCTCCTCCACACCCG-3' |
| SEQ ID NO: 77<br>Mutagenic sense strand | 5'-GGACTCCACCTACCCGACAGCCGAGACCTCCTCCACACCCG-3' |
| SEQ ID NO: 78<br>Mutagenic anti-sense strand | 5'-CGGGTGTGGAGGAGGTCTCGGCTGTCGGGTAGGTGGAGTCC-3' |

TABLE 5

Helix capping mutations to improve thermal tolerance.

| Mutant | Native sequence and mutagenic oligonudeotide |
| --- | --- |
| SEQ ID NO: 79<br>E337R-native sense strand | 5'-GCTGAGGAGGCAGAATTCGGCGG-3' |
| SEQ ID NO: 80<br>Mutagenic sense strand | 5'-GCTGAGGAGGCACGCTTCGGCGG-3' |
| SEQ ID NO: 81<br>Mutagenic anti-sense strand | 5'-CCGCCGAAGCGTGCCTCCTCAGC-3' |
| SEQ ID NO: 82<br>N327D-native sense strand | 5'-GGCAACGAGCTCAACGATGATTACTGC-3' |
| SEQ ID NO: 83<br>Mutagenic sense strand | 5'-GGCAACGAGCTCGACGATGATTACTGC-3' |
| SEQ ID NO: 84<br>Mutagenic anti-sense strand | 5'-GCAGTAATCATCGTCGAGCTCGTTGCC-3' |
| SEQ ID NO: 85<br>A405D-native sense strand | 5'-CCGGTGTCCCTGCTCAGGTCGAATCTCAGTCTCCC-3' |
| SEQ ID NO: 86<br>Mutagenic sense strand | 5'-CCGGTGTCCCTGATCAGGTCGAATCTCAGTCTCCC-3' |
| SEQ ID NO: 87<br>Mutagenic anti-sense strand | 5'-GGGAGACTGAGATTCGACCTGATCAGGGACACCGG-3' |

TABLE 5-continued

Helix capping mutations to improve thermal tolerance.

| Mutant | Native sequence and mutagenic oligonucleotide |
|---|---|
| SEQ ID NO: 88<br>Q410R-native sense strand | 5'-GCTCAGGTCGAATCTCAGTCTCCCAACGCC-3' |
| SEQ ID NO: 89<br>Mutagenic sense strand | 5'-GCTCAGGTCGAATCTCGCTCTCCCAACGCC-3' |
| SEQ ID NO: 90<br>Mutagenic anti-sense strand | 5'-GGCGTTGGGAGAGCGAGATTCGACCTGAGC-3' |
| SEQ ID NO: 91<br>N64D-native sense strand | 5'-CCCTATGTCCTGACAACGAGACCTGCGCG-3' |
| SEQ ID NO: 92<br>Mutagenic sense strand | 5'-CCCTATGTCCTGACGACGAGACCTGCGCG-3' |
| SEQ ID NO: 93<br>Mutagenic anti-sense strand | 5'-CGCGCAGGTCTCGTCGTCAGGACATAGGG-3' |
| SEQ ID NO: 94<br>N64D-native sense strand | 5'-GCTCGACCCTATGTCCTGACAACGAGACCTGCGCGAAGAACTGC-3' |
| SEQ ID NO: 95<br>Mutagenic sense strand | 5'-GCTCGACCCTATGTCCTGACGACGAGACTGCGCGAAGAACTGC-3' |
| SEQ ID NO: 96<br>Mutagenic anti-sense strand | 5'-GCAGTTCTTCGCGCAGGTCTCGTCGTCAGGACATAGGGTVGAGC-3' |

Legend for Tables 2, 3, 3b, 4 and 5. Amino acid mutations sites are listed in the left column. The first letter in the designation is the amino acid of the native protein based upon IUPAC convention for one-letter codes for amino acids. The number represents the amino acid location as designated from the start of the mature protein (excluding the signal peptide, i.e. QSA . . . ). The letter designation after the number represents the amino acid that will occur as a result of the mutation. For example N64D represents the asparagine at site 64 changed to an aspartic acid. The native sense strand sequence for each site is listed in the right column with the oligonucleotide primers (sense and anti-sense) used to obtain the desired mutation below the native sequence in each case. In addition the codon for the targeted amino acid is bolded and the nucleotide substitutions in the mutagenic primers underlined. In some cases only one nucleotide substitution was required the make the desired change, and in others 2 or 3 substitutions were required. In a few cases, double mutations were made with a single mutagenic oligonucleotide.

BIBLIOGRAPHY

The following references are specifically incorporated herein by reference.

Fagertein et. Al. 1984. FEBS. 1265, 167 (2): 389-315.
von Ossowski, I., Teeri, T., Kalkkinen, N., and Oker-Blom, C., Biochem. Biophysical Comm., 233, 25-29 (1997).
Laymon, R. A., Adney, W. S., Mohagheghi, A., Himmel, M. E., and Thomas, S. R. Appl. Biochem. Biotechnol., 57/58, 389-400 (1996).
Teeri, T. T., (1987) Doctoral Thesis, VTT Publications No. 38.
Reinikainen, T., Rouhonen, L., Nevanen, T., Laaksonen, L., Kraulis, P., Jones, T. A., Knowles, J., and Teeri. T. Proteins, Structure Function Genetics 14, 475-482 (1992).
Penttila, M. E., Andre, L., Lehtovaara, P., Bailey, M., Teeri, T. T., Knowles, J. K. C. Gene 63, 103-112 (1988).
Zurbriggen, B., Bailey, M. J., Penttila, M. E., Poutanen, K., and Linko, M. J. Biotechnol. 13, 267-278 (1990).
Okada, H., Sekiya, T., Yokoyama, K., Tohda, H., Kumagai, H., and Morikawa, Y., Appl. Microbiol. Biotechnol., 49, 301-308 (1998).
Maras, M., De Bruyn, A., Schraml, J., Herdewijn, P., Clacyssens, M., Fiers, W., and Contreras, R., Eur. J., Biochem., 245, 617-625 (1997). Circular Dichroism of Proteins
BoXu, Y., and Qing, S. Y. (1997) J. Protein Chem. 16, 107-111.
Lassig, F., Schultz, M. D., Gooch, M., Evans, B. R., and Woodward, J. (1995) Arch. Biochem. Biophys. 322, 119-126.
Pentilla, M. E., Andre, L., Lehtovaara, P., Bailey, M., Teeri, T. T., and Knowles, J. K. C. (1988) Gene 63, 103-112.
Shoemaker, S. P. (1984), In 'The cellulase system of Trichoderma reesei: Trichoderma strain improvement and expression of Trichoderma cellulases in yeast' pp 593-600.
Van Arsdell, J. N., Kwok, S., Schweickart, V. L., Gelfand, D. H., and Innis, M. a. (1987) Bio/Technology 5, 60-64.
Richardson, J. S. & Richardson, D. C. Amino acid preferences for specific locations at the ends of alpha helices [published erratum appears in Science 1988 Dec. 23; 242(4886):1624]. Science 240, 1648-1652 (1988).
Presta, L. G. & Rose, G. D. Helix signals in proteins. Science 240, 1632-1641 (1988).
Nicholson, H., Anderson, D. E., Dao-pin, S. & Matthews, B. W. Analysis of the interaction between charged side chains and the alpha-helix dipole using designed thermostable mutants of phage T4 lysozyme. Biochemistry 30, 9816-9828 (1991).
Motoshima, H. et al. Analysis of the stabilization of hen lysozyme by helix macrodipole and charged side chain interaction. J. Biochem. (Tokyo) 121, 1076-1081 (1997).

Stites, W. E., Meeker, A. K. & Shortle, D. Evidence for strained interactions between side-chains and the polypeptide backbone. J. Mol. Biol. 235, 27-32 (1994).

Jacobson, R. H., Matsumura, M., Faber, H. R. & Matthews, B. W. Structure of a stabilizing disulfide bridge mutant that closes the active-site cleft of T4 lysozyme. Protein Science 1, 46-57 (1992).

Pjura, P. E., Matsumura, M., Wozniak, J. A. & Matthews, B. W. Structure of a thermostable disulfide-bridge mutant of phage T4 lysozyme shows that an engineered cross-link in a flexible region does not increase the rigidity of the folded protein. Biochemistry 29, 2592-2598 (1990).

Sakon, J., Adney, W. S., Himmel, M. E., Thomas, S. R. & Karplus, P. A. Crystal structure of thermostable family 5 endocellulase E1 from *Acidothermus cellulolyticus* in complex with cellotetraose. Biochemistry 35, 10648-10660 (1996).

Russell, R. J. M., Hough, D. W., Danson, M. J. & Taylor, G. L. The crystal structure of citrate synthase from the thermophilic Archaeon, *Thermoplasma acidophilum*. Structure 2, 1157-1167 (1994).

Modeling and measurements of fungal growth and morphology in submerged fermentations. Cui, Y Q; Okkerse, W J; vanderLans, RGJM; Luyben, KCAM. Biotechnol. Bioeng. Oct. 20, 1998 v60 i2 p 216-229 (14).

*Agrobacterium tumefaciens*-mediated transformation of filamentous fungi. deGroot, M J A; Bundock, P; Hooykaas, P J J; Beijersbergen, A G M. Nature Biotechnol. September 1998 v16 i9 p 839-842 (4).

Effect on thermostability and catalytic activity of introducing disulfide bonds into *Aspergillus awamori* glucoamylase. Li, Y X; Coutinho, P M; Ford, C. Protein Eng. August 1998 v11 i8 p 661-667 (7).

Expression and secretion of defined cutinase variants by *Aspergillus awamori*. VanGemeren, I A; Beijersbergen, A; van den Hondel, CAMJJ; Verrips, C T. Appl. Environ. Microbiol. August 1998 v64 i8 p 2794-2799 (6).

Aspects of the use of complex media for submerged fermentation of *Aspergillus awamori*. Cui, Y Q; Ouwehand, J N R; vanderLans, RGJM; Giuseppin, M L F; Luyben, KCAM. Enzyme Microbial Technol. July-August 1998 v23 i1-2 p 168-177 (10).

Influence of fermentation conditions and scale on the submerged fermentation of *Aspergillus awamori*. Cui, Y Q; vanderLans, RGJM; Giuseppin, M L F; Luyben, KCAM. Enzyme Microb. Technol. July-August 1998 v23 i1-2 p 157-167 (11).

Intrinsic kinetic parameters of the pellet forming fungus *Aspergillus awamori*. Hellendoom, L; Mulder, H; van den Heuvel, J C; Ottengraf, S P P. Biotechnol. Bioeng. Jun. 5, 1998 v58 i5 p 478-485 (8).

Protein engineering of *Aspergillus awamori* glucoamylase to increase its pH optimum. Fang, T Y; Ford, C. Protein Eng. May 1998 v11 i5 p 383-388 (6).

Extracellular proteolytic processing of *Aspergillus awamori* GAI into GAII is supported by physico-chemical evidence. Nascimento, H J; Soares, V F; Bon, E P S; Silva, J G. Appl. Biochem. Biotechnol. Spring 1998 v70-2 p 641-650 (10).

Production of xylanase by *Aspergillus awamori* on synthetic medium in shake flask cultures. Siedenberg, D; Gerlach, S R; Schugerl, K; Giuseppin, M L F; Hunik, J. Process Biochem. March 1998 v33 i4 p 429-433 (5).

Influence of morphology on product formation in *Aspergillus awamori* during submerged fermentations. Johansen, C L; Coolen, L; Hunik, J H. Biotechnol. Progress. March-April 1998 v14 i2 p 233-240 (8).

Effects of dissolved oxygen tension and mechanical forces on fungal morphology in submerged fermentation. Cui, Y Q; vander Lans, RGJM; Luyben, KCAM. Biotech. Bioeng. Feb. 20, 1998 v57 i4 p 409-419 (11).

Effect of introducing proline residues on the stability of *Aspergillus awamori*. Li, Y X; Reilly, P J; Ford, C. Protein Eng. October 1997 v10 i10 i10 p 1199-1204 (6).

The ER chaperone encoding bipA gene of black *Aspergilli* is induced by heat shock and unfolded proteins. vanGemeren, I A; Punt, P J; DrintKuyvenhoven, A; Broekhuijsen, M P; vantHoog, A; Beijersbergen, A; Verrips, C T; van den Hondel, CAMJJ. Gene. Oct. 1, 1997 v198 i1-2 p 43-52 (10).

Effect of agitation intensities on fungal morphology of submerged fermentation. Cui, Y Q; vanderLans, RGJM; Luyben, KCAM. Biotech. Bioeng. Sep. 5, 1997 v55 i5 p 715-726 (12).

Characterization of the bip gene of *Aspergillus awamori* encoding a protein with an HDEL retention signal homologous to the mammalian BiP involved in polypeptide secretion. Hijarrubia, M J; Casqueiro, J; Gutierrez, S; Fernandez, F J; Martin, J F. Current Genetics. August 1997 v32 i2 p 139-146 (8).

Expression and functional analysis of a hyperglycosylated glucoamylase in a parental host, *Aspergillus awamori* var. *kawachi*. Goto, M; Ekino, K; Furukawa, K. Appl. Environ. Microbiol. July 1997 v63 i7 p 2940-2943 (4).

Glucoamylase gene fusions alleviate limitations for protein production in *Aspergillus awamori* at the transcriptional and (post)translational levels. Gouka, R J; Punt, P J; van den Hondel, CAMJJ. Appl. Environ. Microbiol. February 1997 v63 i2 p 488-497 (10).

Kinetics of mRNA and protein synthesis of genes controlled by the 1,4-beta-endoxylanase A promoter in controlled fermentations of *Aspergillus awamori*. Gouka, R J; Stam, H; Fellinger, A J; Muijsenberg, RJGT; vandeWijngaard, A J; Punt, P J; Musters, W; van den Hondel, CAMJJ. Appl. Environ. Microbiol. October 1996 v62 i10 p 3646-3649 (4).

An expression system based on the promoter region of the *Aspergillus awamori* 1,4-beta-endoxylanase A gene. Gouka, R J; Hessing, J G M; Punt, P J; Stam, H; Musters, W; van den Hondel, CAMJJ. Appl. Microbiol. Biotechnol. (1996) v46 µl p 28-35 (8).

The effect of pre- and pro-sequences and multicopy integration on heterologous expression of the *Fusarium* solani pisi cutinase gene in *Aspergillus awamori*. vanGemeren, I A; Beijersbergen, A; Musters, W; Gouka, R J; vandenHondel, CAMJJ; Verrips, C T. Appl. Microbiol. Biotechnol. (1996) v45 i6 p 755-763 (9).

Analysis of heterologous protein production in defined recombinant *Aspergillus awamori* strains. Gouka, R J; Punt, P J; Hessing, J G M; van den Hondel, CAMJJ. Appl. Environ. Microbiol. (1996) v62 i6 p 1951-1957 (7).

Effect of replacing helical glycine residues with alanines on reversible and irreversible stability and production of *Aspergillus awamori* glucoamylase. Chen, H M; Li, Y X; Panda, T; Buehler, F; Ford, C; Reilly, P J. Protein Eng. (1996) v9 i6 p 499-505.

The invention claimed is:

1. A nucleic acid molecule having a nucleic acid sequence encoding a variant cellobiohydrolase mutated with respect to a wild-type cellobiohydrolase represented by SEQ ID NO: 99, the mutation providing means for improving cellobiohydrolase functionality with respect to the wild-type cellobiohydrolase functionality, wherein the functionality is thermostability, enzymatic activity, catalytic activity, product inhibition, glycosylation, and/or peptide strain.

2. The nucleic acid molecule of claim 1 wherein the functionality is thermostability and the means for improving comprises proline substituted at position 8.

3. The nucleic acid molecule of claim 2 wherein the means for improving further comprises the helix-capping mutation defined as an arginine or aspartic acid residue substituted at a position selected from the group consisting of position 64, 337, 327, 405, 410, and any combination thereof.

4. The nucleic acid molecule of claim 2 wherein the means for improving further comprises substitution of glycine at position 99.

5. A method for mutating a nucleic acid encoding a wild type cellobiohydrolase of SEQ ID NO: 99, the method comprising mutating the wild type cellobiohydrolase with proline substituted at position 8.

6. The method of claim 5, wherein the mutation further comprises substitution of a non-glycosyl accepting amino acid residue in place of an N-glycosylation site amino acid residue at a position selected from the group consisting of position 45, 270, 384, and any combination thereof.

7. The method of claim 5, wherein the step of mutating comprises site-directed mutagenesis.

8. The method of claim 5, further comprising a step of shortening a linker region of the wild-type cellobiohydrolase with respect to wild-type linker region SEQ ID NO: 2 to provide a linker region having a length of from about 6 amino acids to about 17 amino acids located between a catalytic domain and a cellulose binding domain (CBD) of SEQ ID NO: 99.

9. The nucleic acid molecule of claim 2 wherein the functionality is thermostability and the means for improving further comprises substitution of a cysteine at positions 197 and 370.

10. The nucleic acid molecule of claim 2 wherein the functionality is thermostability and the means for improving further comprises substitution of a non-glycosyl accepting amino acid residue in place of an N-glycosylation site amino acid residue at a position selected from the group consisting of position 45, 270, 384, and any combination thereof.

11. The nucleic acid molecule of claim 2 wherein the functionality is thermostability and the means for improving further comprises substitution of an alanine at a position selected from the group consisting of position 45, 270, 384, and any combination thereof.

12. The nucleic acid molecule of claim 1, wherein the variant cellobiohydrolase comprises a linker region having a length of from about 6 amino acids to about 17 amino acids located between a catalytic domain and a cellulose binding domain (CBD) and wherein the variant cellobiohydrolase comprises a proline substituted at position 8 relative to SEQ ID NO: 99.

13. A nucleic acid molecule having a nucleic acid sequence encoding a variant cellobiohydrolase mutated with respect to a wild-type cellobiohydrolase of SEQ ID NO: 99, the mutation comprising proline substituted in the place of the serine at position 8.

14. The nucleic acid molecule of claim 1 wherein the means for improving functionality comprises means for enhancing thermostability.

15. The nucleic acid molecule of claim 13, wherein the variant cellobiohydrolase is further mutated with a mutation selected from the group consisting of:
   (a) proline substituted at a position selected from the group consisting of position 27, 43, 75, 94, 190, 195, 287, 299, 312, 315, 359, 398, 401, 414, 431, 433, and any combination thereof;
   (b) a helix-capping mutation defined as an arginine or aspartic acid residue substituted at a position selected from the group consisting of position 64, 337, 327, 405, 410 and any combination thereof;
   (c) substitution of glycine at position 99;
   (d) substitution of cysteine at positions 197 and 370;
   (e) substitution of a non-glycosyl accepting amino acid residue in place of an N-glycosylation site amino acid residue at a position selected from the group consisting of position 45, 270, 684 and any combination thereof,
   (f) alanine substitution at a position selected from the group consisting of position 45, 270, 384 and any combination thereof; and
   (g) any combination of the mutations of (a), (b), (c), (d), (e), (f),
   wherein the positional reference is within the amino acid sequence of the wild-type cellobiohydrolase SEQ ID NO: 99.

16. A nucleic acid molecule having a nucleic acid sequence encoding a variant cellobiohydrolase mutated with respect to a wild-type cellobiohydrolase represented by SEQ ID NO: 99, wherein the mutation comprises a proline substituted at position 8, and wherein the proline substitution improves the functionality of the variant cellobiohydrolase with respect to the wild-type cellobiohydrolase by improving thermostability.

17. The nucleic acid molecule of claim 16 wherein the mutation further comprises an arginine or aspartic acid residue substituted at a position selected from the group consisting of position 64, 337, 327, 405, 410, and any combination thereof.

18. The nucleic acid molecule of claim 16 wherein the mutation further comprises substitution of glycine at position 99.

19. The nucleic acid molecule of claim 16 wherein the mutation further comprises substitution of a cysteine at positions 197 and 370.

20. The nucleic acid molecule of claim 16 wherein the mutation further comprises substitution of a non-glycosyl accepting amino acid residue in place of an N-glycosylation site amino acid residue at a position selected from the group consisting of position 45, 270, 384, and any combination thereof.

* * * * *